Figure 1:
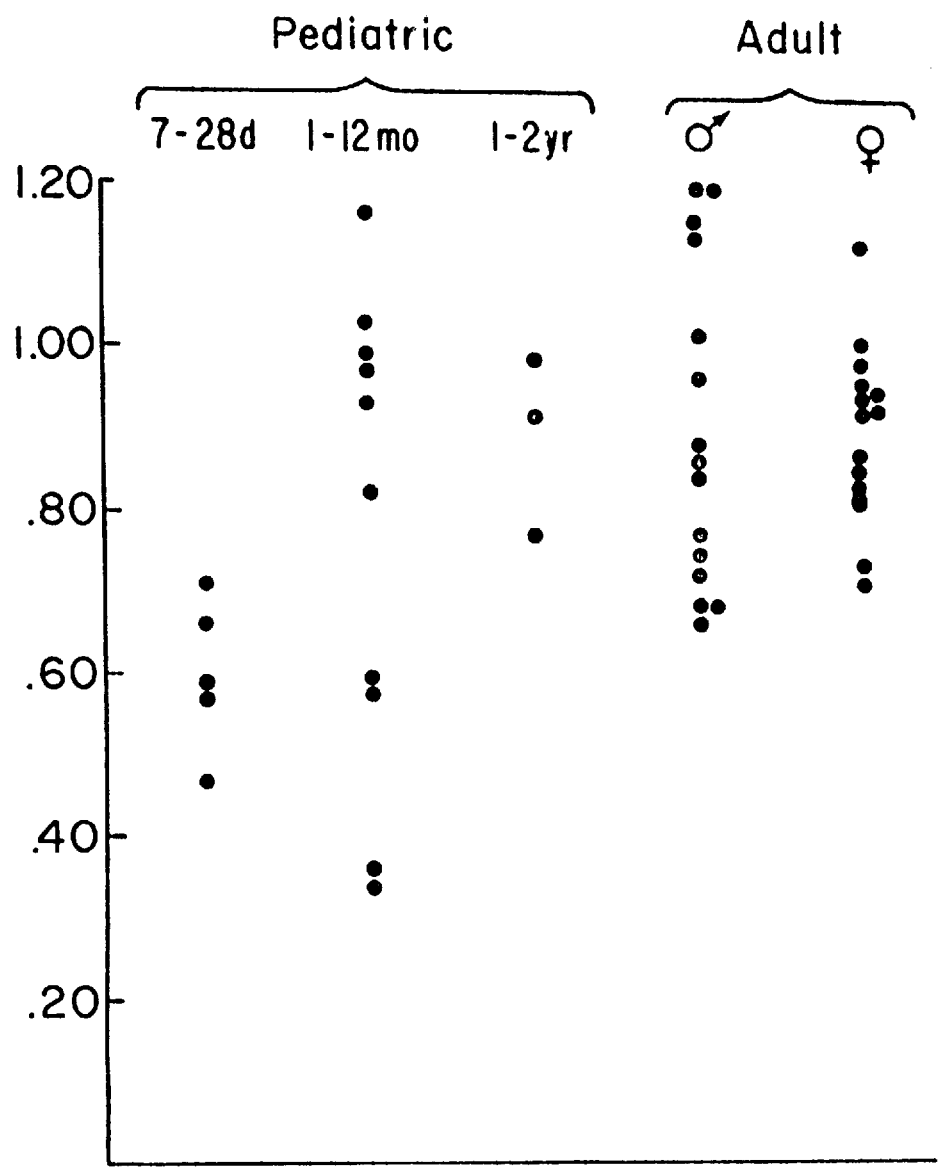

United States Patent [19]

Rodman

[11] Patent Number: 5,872,012
[45] Date of Patent: Feb. 16, 1999

US005872012A

[54] PROTAMINE-REACTIVE IGM ANTIBODIES

[75] Inventor: Toby C. Rodman, New York, N.Y.

[73] Assignee: The Institute for Human Genetics and Biochemistry, Geneva, Switzerland

[21] Appl. No.: 271,210

[22] Filed: Jul. 5, 1994

Related U.S. Application Data

[63] Continuation of Ser. No. 88,602, Jul. 6, 1993, abandoned, which is a continuation of Ser. No. 924,412, Jul. 30, 1992, abandoned, which is a continuation of Ser. No. 173,705, Mar. 25, 1988, abandoned.

[51] Int. Cl.$^6$ .................................................. G01N 33/53
[52] U.S. Cl. .................. 436/518; 435/7.92; 435/974; 435/975; 436/548; 436/808; 530/329; 530/330; 530/358; 530/387.9; 530/852; 530/863
[58] Field of Search ............................... 435/5, 7.1, 7.92, 435/69.1, 974, 975; 436/518, 512, 528, 547, 548, 808, 811, 816; 530/300, 329–331, 333, 358, 852, 387.9, 863, 810–812

[56] References Cited

U.S. PATENT DOCUMENTS 4,699,877  10/1987  Cline et al. .................................. 435/6

OTHER PUBLICATIONS

Rodman et al, "Naturally Occurring Antibodies Reactive with Sperm Proteins: Apparent Deficiency in Aids Sera", *Science*, vol. 228, No. 4704 (7 Jun. 1985) pp. 1211–1215.

Rodman et al, "Reactivity of Natural LgM Antibodies with Sperm Head Surface Proteins –Use of ELISA to Characterize the Reaction", *Journal of Immunological Methods*, vol. 94, (1986) pp. 105–111.

Rodman et al, "Protamine–Reactive Natural LgM Antibodies in Human Sera", *Journal of Experimental Medicine*, vol. 167 No. 3 (Mar. 1, 1988), pp. 1228–1246.

Chemical Abstract 107 (15): 132233 "Monoclonal Antibodies to Human protamine" in Hybridoma 1987, 6(3) 313–20.

Chemical Abstract 109 (1): 4921, "Detection of the Major Epitopes of Human Protamine Pl Recognized by Rabbit and Mouse Antibodies" in *Mol. Immunol* 25(4) 403–10, 1988.

Roitt et al, *Immunology* (C.V. Mosby Company St. Louis) 1985, pp. 6.5–66.

Biological Abstract 78: 11446.

Rodman et al, Clin. Immunol. Immunopathol. 571 430–440 (1990).

Rodman et al, Proc. Natl. Acad. Sci., USA, 90: 7719–7723 (1993).

Morcos et al, "Reactivated Movement of Decondensed Rat Sperm Models and a Description of their Ultrastructure," J. of Exp. Zoology 270: 388–398 (1994).

Neits et al, "Direct Measurement of Antibody Affinity Distribution by Hapten–Inhibition Enzyme Immunoassay," Mol. Immunol. 21(6):537–543 (1984).

(List continued on next page.)

*Primary Examiner*—Carol A. Spiegel
*Attorney, Agent, or Firm*—Darby & Darby

[57] ABSTRACT

The present invention is directed to protamine-reactive, IgM antibodies, and their uses in prognosis, diagnosis, and therapy. In a specific embodiment, the invention relates to low affinity binding, protamine-reactive serum IgM antibodies. In particular, such antibodies can recognize a sequence comprising four arginyl residues, including a triplet, within a six amino acid residue sequence. Such antibodies may be natural antibodies (i.e., not induced). A low affinity subset of serum protamine-reactive IgM antibodies may be assayed for prognosis or diagnosis of AIDS. Such antibodies are detectable in sera of normal subjects and HIV-infected individuals who subsequently exhibit a significant period of latency, but are absent or deficient in sera of individuals diagnosed with AIDS and sera of HIV infected individuals, who though asymptomatic at the time of the sampling, proceed to AIDS within a relatively short time. The invention provides methods and diagnostic kits for the detection and/or measurement of the low affinity subset of protamine-reactive serum IgM antibodies, for the prognosis and diagnosis of AIDS and other immune system abnormalities.

6 Claims, 14 Drawing Sheets

OTHER PUBLICATIONS

Benner et al., 1982, Immunology Today, 9:243–249.
Chow et al., 1981, Int. J. Cancer 27:459–469.
Jerne, Niels K., 1955, Bacteriology 41:849–857.
Kolk and Samuel, Biochim. Biophys. Acta 393:307–319 (1975).
Rodham et al., J. Cell Biol. 80:605–620 (1979).
Samuel, Immunol. Comm. 9(3):283–288 (1980).
Rodman et al., J. Cell Sci. 53:227–244 (1982).
Rodman et al., Gamete Res. 8:129–147 (1983).
Rodman et al., Exp. Cell Res. 150:269–281 (1984).
Ammer et al., Biol. Chim. Hoppe–Seyler 367:515–522 (1986).
McKay et al., Eur. J. Biochem. 156:5–8 (1986).
Pruslin et al., Gamete Res. 18:179–190 (1987).
Hald et al., J. Repro. Fert. 10:15–26 (1987).
Stanker et al., Hybridoma 6(3):293–303 (1987).
Roux et al., J. Repro. Fert. 82:35–42 (1988).
Dighiero et al., J. Immunol 134:765–771 (1985).
Tongio et al., Tissue Antigens 26:271–285 (1985).
Cohen and Cooke, Immun. Today 7(12): 363–364 (1986).
Gottlieb et al., N. Engl. J. Med. 305:1425–1431 (1981).
Masur et al., N. Engl. J. Med. 305:1431–1438 (1981).
Barre–Sinoussi et al., Science 220:868–871 (1983).
Gallo et al., Science 224:500–503 (1984).
Feorino et al., Science 225:69–72 (1984).
Levy et al., Science 225:840–842 (1984).
Klatzman et al., Nature 312:767–768 (1984).
Dalgleish et al., Nature 312:763–766 (1984).
Goedert et al., Lancet ii:711–716 (1984).
Mavligit et al., J. Am. Med. Assoc. 251:237–247 (1984).
Ranki et al., Cancer Res. 45:4616S–4618S (1985).
McDougal et al., Science 231:382–385 (1986).
Maddon et al., Cell 47:333–348 (1986).
Ratnam et al., Aust. N.Z.J. Med. 15:757–760 (1986).
Darrow et al., Am. J. Pub. Hlth. 77:479–483 (1987).
Kingsley et al., Lancet ii:345–348 (1987).
Adams et al., Clin. Immunol. Immunopath. 46:442–449 (1988).
Morrison et al., Proc. Natl. Acad. Sci. USA 81:6851–6855 (1984).
Takeda et al., Nature 314:452–454 (1985).
Pruslin et al., J. Immunol. Meth. 94:99–103 (1986).
DeLange et al., Proc. Natl. Acad. Sci. USA 69:882–884 (1972).
Shoenfeld et al., Arthritis Rheum. 30:169–175 (1987).
Dyrberg and Oldstone, J. Exp. Med. 164:1344–1349 (1986).
Geysen et al., Science 235:1184–1190 (1987).

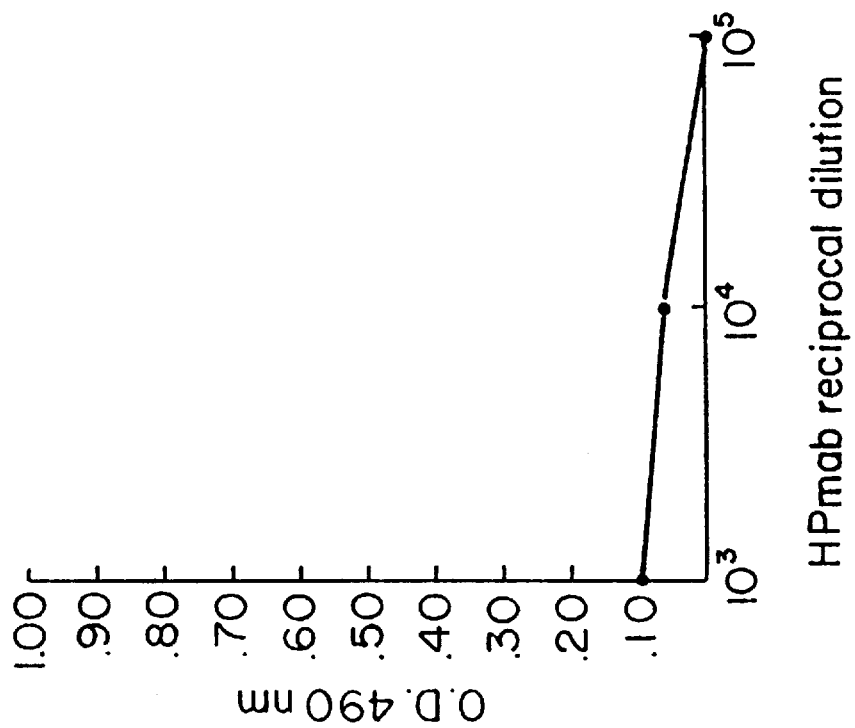
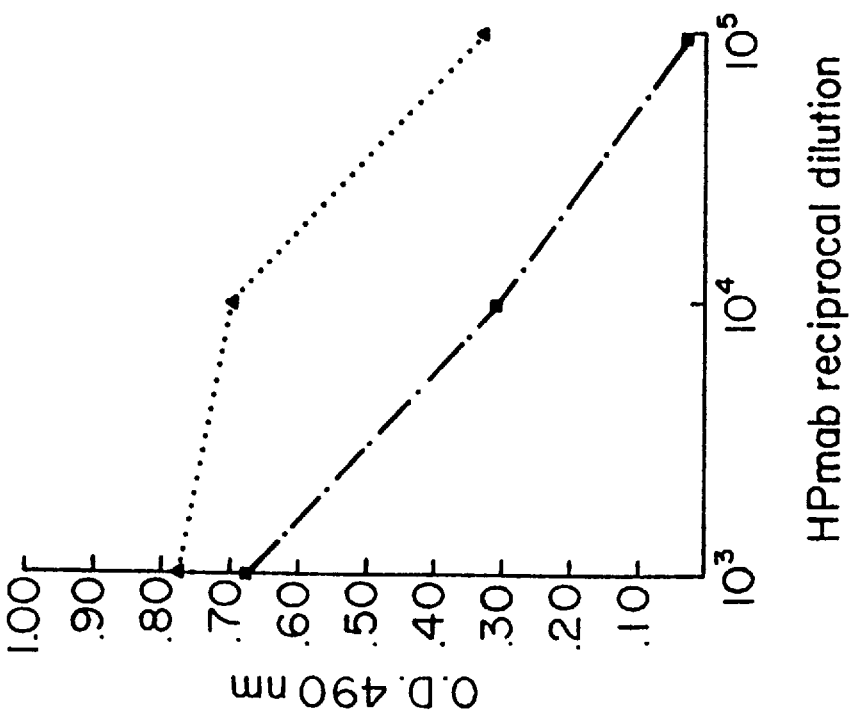

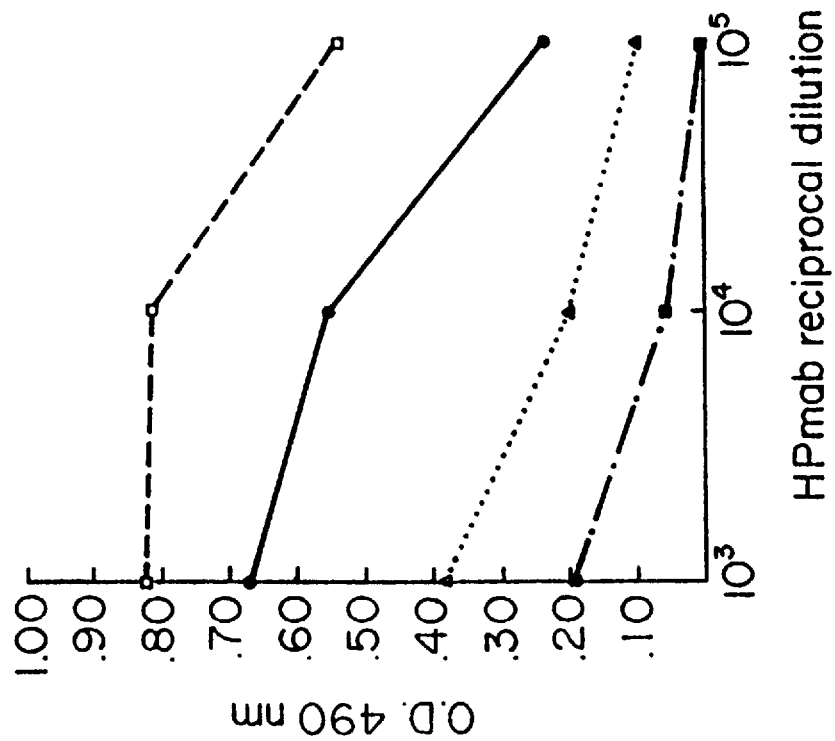
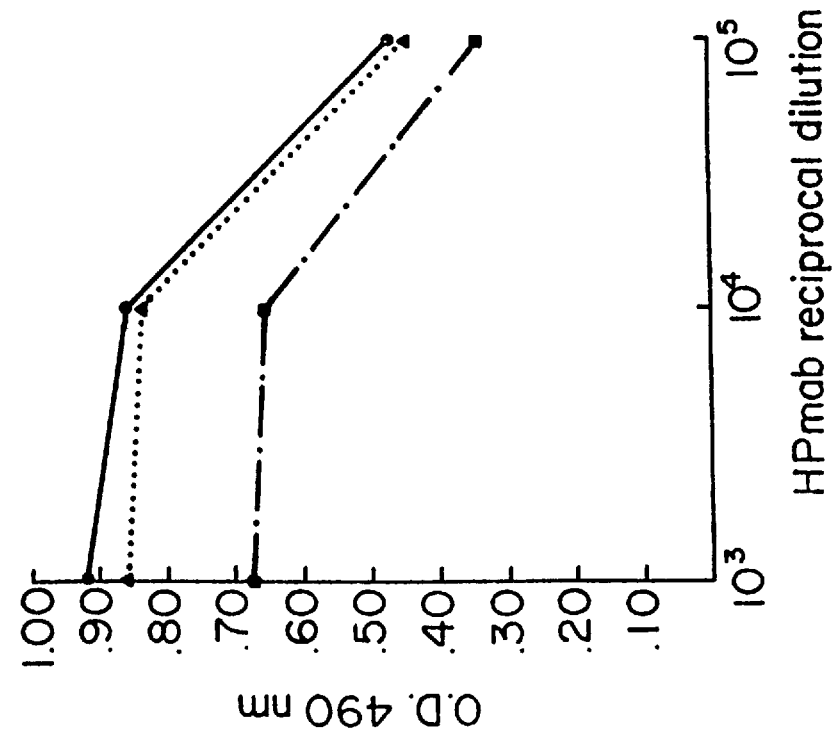

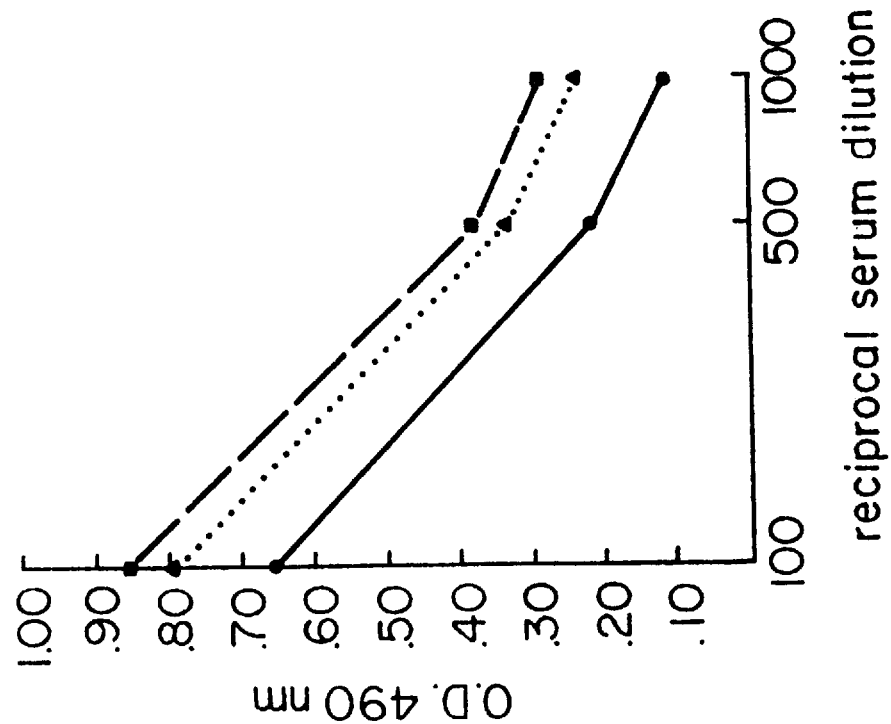
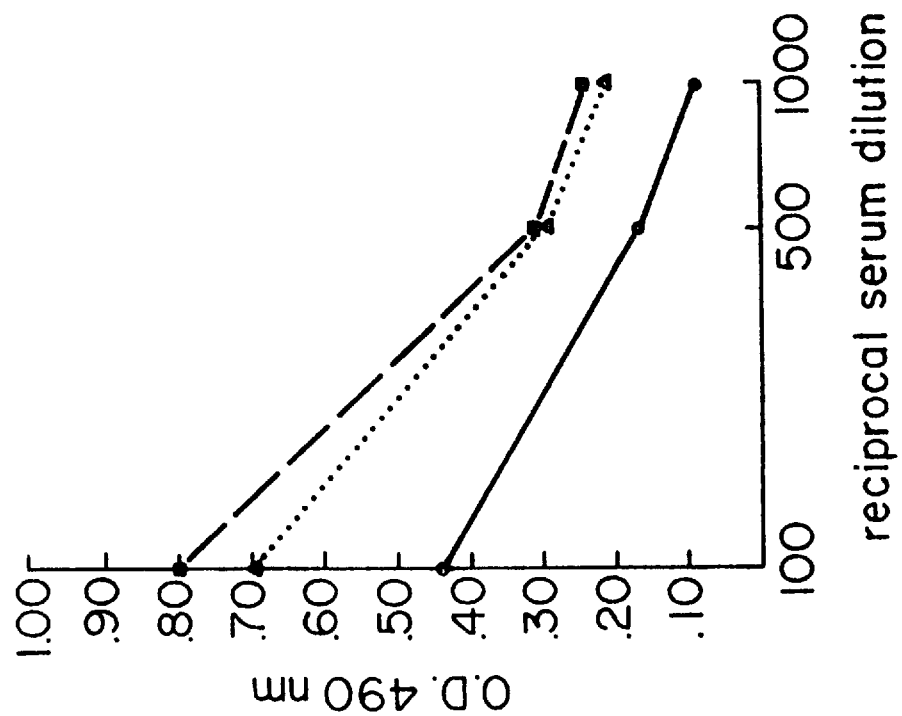

RECIPROCAL SERUM DILUTION

RECIPROCAL SERUM DILUTION

RECIPROCAL SERUM DILUTION

RECIPROCAL SERUM DILUTION

PROTAMINE-REACTIVE IGM ANTIBODIES

This is a continuation of application Ser. No. 08/088,602 (now abandoned), filed Jul. 6, 1993, which is a continuation of Ser. No. 07/924,412 filed Jul. 30, 1992 (now abandoned), which is a continuation of Ser. No. 07/173,705 filed Mar. 25, 1988 (now abandoned).

TABLE OF CONTENTS

1. Introduction
2. Background of the Invention
2.1. Protamines
2.2. Natural Antibodies
2.3. Acquired Immunodeficiency Syndrome
3. Summary of the Invention
3.1. Definitions
4. Description of the Figures
5. Detailed Description of the Invention
5.1. Protamine-Reactive IgM Antibodies
5.2. Use in Prognostics and Diagnostics: Prediction of Latency from HIV Infection to Manifestation of AIDS
5.3. Assays of Serum Protamine-Reactive IgM Antibodies
   5.3.1. Assay Sytems
   5.3.2. Antigens
   5.3.3. Assay Method for Prediction of HIV Latency Period
5.4. Therapy
5.5. Diagnostic Kits
6. Example: Protamine-Reactive Natural IgM Antibodies in Human Sera
  6.1. Materials and Methods
    6.1.1. Enzyme-linked Immunosorbent Assay for Serum Antibodies
    6.1.2. Antigens
    6.1.3. Monoclonal Antibodies
    6.1.4. Human Sera
    6.1.5. Immunoabsorptions
    6.1.6. Homology Search
  6.2. Results
    6.2.1. Protamine-Reactive Antibodies Occur in Human Sera
    6.2.2. Identification of Human Sperm Protamines
    6.2.3. Specificity of Anti-Protamine Monoclonal Antibody for Protamines Definition of the Epitope
    6.2.4. Protamine-Reactive IgM Antibodies
    6.2.5. Antigenic Sites Recognized by HPmAb and Human Serum Immunoglobulin Antibodies are Similar and Perhaps Identical
  6.3. Discussion
7. Example: Low-Affinity Protamine-Reactive IgM Antibodies Present in Human Sera are Related to Human Immunodeficiency Virus Latency
  7.1. The Presence in Normal and Absence from AIDS' Patients' Sera of Low Affinity Protamine-Reactive IgM Antibodies
  7.2. A Quantitation of Anti-Protamine Antibodies for Prediction of HIV Latency
  7.3. Confirmation of the Existence of a Low-Affinity Subset of Protamine-Reactive Antibodies
  7.4. Pediatric Sera Contain a Population of Protamine-Reactive IgM Antibodies That Is Homogenous in Binding Affinity
  7.5. Naturally Occurring Anti-Protamine Antibodies
8. Deposit of Hybridoma

1. INTRODUCTION

The present invention relates to protamine-reactive, IgM antibodies, and their uses in prognosis, diagnosis, and therapy. In particular, the invention relates to protamine-reactive serum IgM antibodies which can recognize a sequence comprising four arginyl residues, including a triplet, within a six amino acid residue piece, and which exhibit low binding affinity to antigen. This low affinity antibody subset of protamine-reactive serum IgM antibodies may be assayed for prognosis or diagnosis of AIDS. Methods and diagnostic kits for the detection and/or measurement of the low affinity protamine-reactive serum IgM antibodies are provided.

2. BACKGROUND OF THE INVENTION

2.1. Protamines

Protamines are small highly basic nucleoproteins associated with DNA that occur in no cells other than spermatids and spermatozoa. Those proteins are synthesized de novo and incorporated into the nuclei of spermatogenic cells during spermiogenesis where they replace histones and are bound to the spermatozoal DNA, a progression that takes place in the immunologically sequestered lumena of the seminiferous tubules of the postpuberal testis (Gilula, N. B., et al., 1976, Dev. Biol. 50:142).

Protamine 1 (originally termed p15) is a human protamine that occurs in four variants. It was identified and characterized by use of a monoclonal antibody (termed HPmAb, described infra) (Rodman, T. C., et al., 1983, Gamete Res. 8:129–147).

Human protamine 2 has long been recognized and known to occur as two variants (Kolk, A. H. and Samuel, T., 1975, Biochim. Biophys. Acta 393:307–319), later designated as protamine 2a and 2b (McKay, D. J., et al., 1986, Eur. J. Biochem. 156:5–8).

Polyvalent rabbit antisera specific for the two protamines of mouse sperm chromatin have been isolated and used to characterize the protamines as to distribution and DNA association, and to recognize immunochemical cross-reactivity among mammalian protamines (Rodman, T. C., et al., 1984, Exp. Cell Res. 150:269–281).

Polyclonal rabbit antisera against human protamines have been used in immunohistochemical studies of histone to protamine transition during spermiogenesis (Roux, Ch., et al., 1988, J. Reprod. Fert. 82:35–42). The detection steps of the immunoassays in this study were carried out by use of antibodies against rabbit IgG.

Mouse monoclonal antibodies to human protamines of the IgG1 and IgG2b isotypes have been isolated and partially characterized (Stanker, L. H., et al., 1987, Hybridoma 6(3): 293–303). None of the described antibodies reacted with polyarginine.

Autoantibodies against spermatozoal antigens have been detected in vasectomized males, by Western blotting procedures assaying for antibodies reactive with spermatozoal antigens separated by SDS-polyacrylamide gel electrophoresis, or by agglutination tests (Hald, J., et al., 1987, J. Reprod. Immunol. 10:15–26). Since protamines are too basic to migrate in SDS-polyacrylamide gels, and have immunoreactive sites which are not accessible unless the chromatin is decondensed (Rodman, T. C., et al., 1970, J.

Cell Biol. 80:605–620), the reported assays did not detect anti-protamine antibodies.

2.2. Natural Antibodies

The natural antibody repertoire is a segment of the immune system that is little understood, was early postulated to provide a first defense against specific infectious agents (Michael, J. G., 1969, Curr. Top. Microbiol. Immunol. 48:43–62), and has recently been the subject of increased interest and conjecture of a possible role in control of autoimmunity (Cohen, I., et al., 1986, Immunol. Today 7:363–364) or other phases of immunoregulation (Dighiero, G., et al., 1985, J. Immunol. 134:765). Natural antibodies frequently have been designated as those of lower affinity than their induced counterparts (see e.g., Day, E. D., et al., 1986, J. Neuroimmunol. 13:143–158; Hoch, S., et al., 1986, J. Immunol. 136:892–897; Tongio, M. M., et al., 1985, Tissue Antigens 26:27–285).

2.3. Acquired Immunodeficiency Syndrome

Acquired Immunodeficiency Syndrome (AIDS) is a disease which is characterized by a severe immune deficiency primarily caused by a decreased cell-mediated immune response (Gottlieb, M., et al., 1981, N. Engl. J. Med. 305:1425; Masur, J., et al., 1981, N. Engl. J. Med. 305:1431). The immunodeficient state is characterized by a decrease in $T_H$ (T helper) lymphocytes, a reversal of the normal CD4 $(T4)^+$:CD8 $(T8)^+$ cell ratio, lymphopenia, an increased incidence of opportunistic infections (e.g., *Pneumocystis carinii* pneumonia), and/or malignancy (e.g., lymphoma or Kaposi's sarcoma). The syndrome is usually fatal.

The causative agent of AIDS is a retrovirus, now termed Human Immunodeficiency Virus (HIV) (also isolated as LAV/ARV/HTLV III) which infects $T_H$ lymphocytes (Gallo, R. C., et al., 1984, Science 224:500; Barre-Sinoussi, F., et al., 1983, Science 220:868; Feorino, P. M., et al., 1984, Science 225:69; Levy, J. A., et al., 1984, Science 225:840).

The CD4 T cell surface molecule has been identified as a receptor for the virus, and the virus' subsequent cytolytic activity depletes that cell population (Klatzman, D., et al., 1985, Nature 312:767; Dalgleish, A. G., et al., 1984, Nature 312:763; McDougal, J. S., et al., 1986, Science 231:382; Maddon, P. J., et al., 1986, Cell 47:333).

A patient is diagnosed with AIDS when he or she (1) tests positive for the presence of HIV and presents with one or more of the specific indicator diseases (neoplasms, opportunistic infections) or (2) in the absence of laboratory evidence for HIV infection, all other causes of immunodeficiency are ruled out and one of the indicator diseases is present together with a low (less than 400/mm$^3$ CD4 $^+$ T lymphocyte count. AIDS-related complex (ARC) refers to those patients testing positive for HIV and presenting with persistent generalized lymphadenopathy, long-lasting fever, weight loss, persistent diarrhea, or extreme lassitude, but who have not yet developed one of the indicator diseases associated with full-blown AIDS.

A number of studies have established that a signficant risk-for-AIDS factor is that of receptive anal intercourse (see e.g., Goedert, J. J., et al., 1984, Lancet ii:711–716; Darrow, W. W., et al., 1987, Am. J. Pub. Health 77:479–483; Kingsley, L. A., et al., 1987, Lancet ii:345–348). The increased risk is generally attributed to efficiency of transmission of the virus by that route. Some consideration, however, has been given to the possible implication of seminal components in the pathologic consequences of HIV infection (Mavligit, G. M., et al., 1984, J. Am. Med. Assoc. 251:237–241; Ranki, A., et al., 1985, Cancer Res. 45:4616S–18S; Ratman, K. V., et al., 1986, Aust. N. Z. J. Med. 15:757–760). Relevant to that may be a recent report that the mean latency period of HIV infected hemophiliacs is considerably longer than that for other HIV infected groups (Ekert, H., 1987, Nature 329:494).

Adams et al. (1988, Clin. Immunol. Immunopathol. 45:442–449) have reported that there is significant incidence of antibodies to sperm and seminal plasma components in sera of ARC and AIDS patients. Antibodies were assayed for by hemagglutination, for antibodies to seminal plasma, and by indirect immunofluorescence on fixed human sperm. Neither of the assay methods used could have detected protamine-reactive antibodies, since protamines are nuclear proteins and thus would not be accessible in seminal plasma for antibody binding and hemagglutination, and since protamine immunoreactive sites are not accessible for antibody binding in immunofluorescent assays unless the sperm chromatin is first decondensed (Rodman, T. C., et al., 1970, J. Cell Biol. 80:605–620; Rodman, T. C., et al., 1984, Exp. Cell. Res. 150:269–281).

3. SUMMARY OF THE INVENTION

The present invention relates to protamine-reactive, IgM antibodies, and their uses in prognosis, diagnosis, and therapy. In a specific embodiment, the invention relates to low affinity binding, protamine-reactive serum IgM antibodies. In particular, such antibodies can recognize a sequence comprising four arginyl residues, including a triplet, within a six amino acid residue sequence. Such antibodies may be natural antibodies (i.e., not induced).

A low affinity subset of serum protamine-reactive IgM antibodies may be assayed for prognosis or diagnosis of AIDS. Such antibodies are detectable in sera of normal subjects and HIV-infected individuals who subsequently exhibit a significant period of latency, but are absent or deficient in sera of individuals diagnosed with AIDS and sera of HIV infected individuals, who though asymptomatic at the time of the sampling, proceed to AIDS within a relatively short time. The invention provides methods and diagnostic kits for the detection and/or quantitative determination of the low affinity subset of protamine-reactive serum IgM antibodies, for the prognosis and diagnosis of AIDS and other immune abnormalities. In a specific embodiment, such a diagnostic kit comprises (a) a peptide comprising a sequence of four arginyl residues, including a triplet, within a six amino acid residue sequence; and (b) a conjugate of a specific binding partner for IgM antibodies and a label capable of producing a detectable signal.

3.1. Definitions

As used herein, the following abbreviations will have the meanings indicated:

AIDS=acquired immunodeficiency syndrome
ARC=AIDS-related complex
BSA=bovine serum albumin
ELISA=enzyme-linked immunosorbent assay
Fv=the variable region or antigen-combining site of an antibody molecule. This may be any fragment which contains the idiotype of the molecule including but not limited to the Fab, F(ab')$_2$, Fab', and the like
HIV=Human Immunodeficiency Virus
HPmAb=a monoclonal antibody to human sperm protamines, as produced by the hybridoma having accession number HB 9668 mAb=monoclonal antibody
P1=purified human protamine 1
P2=purified human protamine 2
PAGE=polyacrylamide gel electrophoresis
PBS=phosphate-buffered saline

4. DESCRIPTION OF THE FIGURES

FIG. 1. Proportionality of protamine-reactive IgM to total IgM in human sera. A value (x) for total IgM for each serum was derived as percentage of a reference serum (see Section 6.1.1) and a value (y) for protamine-reactive IgM was derived as percentage of the same reference serum. The plotted values are x/y for each serum.

Figure 2A:
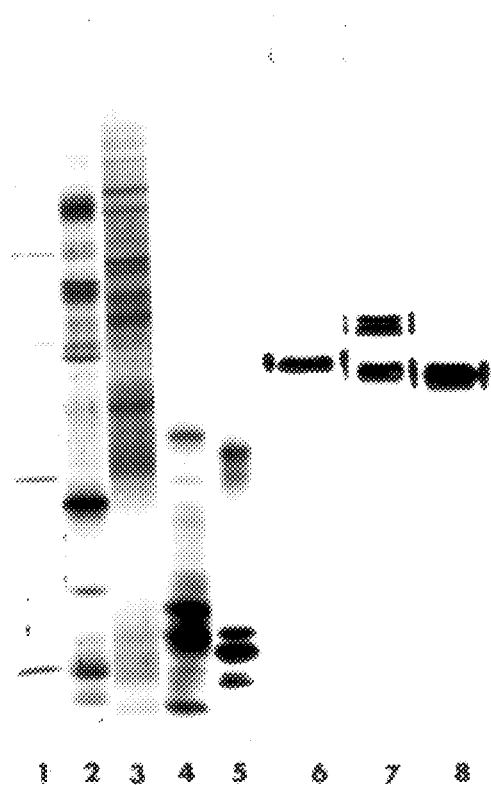
Figure 2B:
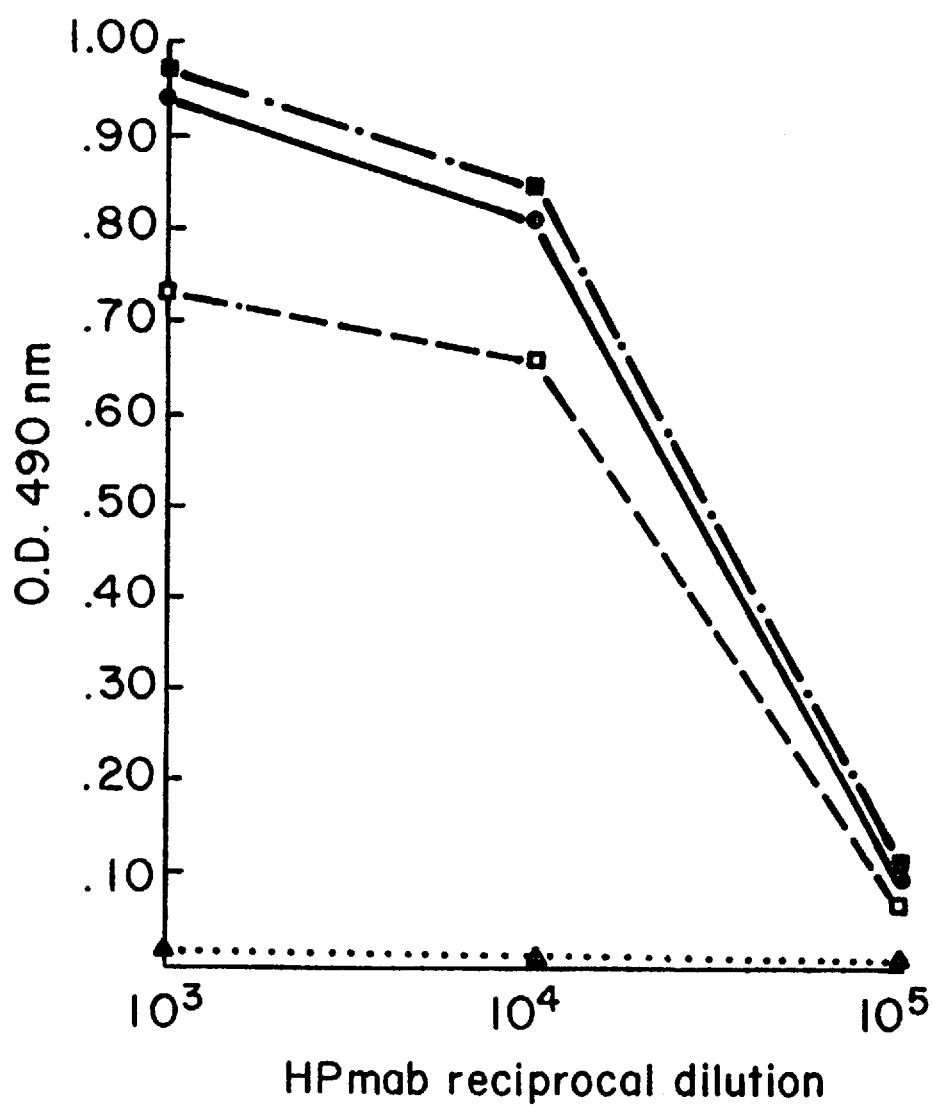

FIG. 2. (A) Fractions of human sperm proteins (Lanes 1–5) SDS PAGE; (lanes 6–8) acetic acid-urea PAGE. (Lane 1) Molecular weight markers: 14.4, 20, 30, 43, 67, 94×10$^3$ daltons (lane 2) tail proteins; (lane 3) TRITON X-100 soluble proteins of head membranes; (lane 4) 8% GuCl eluate of BIOREX-70 chromatogram of nuclear proteins; (lane 5) 16% eluate; (lane 6) 23% eluate (P1); (lane 7) 25% eluate (P1 and phosphorylated P2); (lane 8) 27% eluate (P2). (B) ELISA values of HPmAb reactivity with each sperm protein fraction. (Lanes 2–5)........; (lane 6) —.—.—.—.; (lane 7) ——; (lane 8)--------. HPmAb is reactive only with the three protamine fractions (lanes 6, 7, and 8).

FIG. 3. Reactivity of HPmAb with (A) polyarginine and (B) polylysine at ascending antigen concentrations. 2 μg/ml polyarginine —.—.—.—.; 5, 10, or 20 μg/ml polyarginine ........; 2, 5, 10 or 20 μg/ml polylysine——. Each plotted value represents the mean of four assays, carried out in duplicate.

FIG. 4. Reactivity of HPmAb with (A) P1 at 2 μg/ml —.—.—.—.; 5 μg/ml ........; 10 or 20 μg/ml ——(B) P2 at 2 μg/ml —.—.—.—.; 5 μg/ml ........; 10 μg/ml ——; 20 μg/ml --------. Each plotted value represents the mean of five assays, each carried out in duplicate. With molar equivalents (equivalent weights) of P1 and P2, reactivity of HPmAb is greater with and saturated at lower antigen concentrations of P1.

Figure 5A:
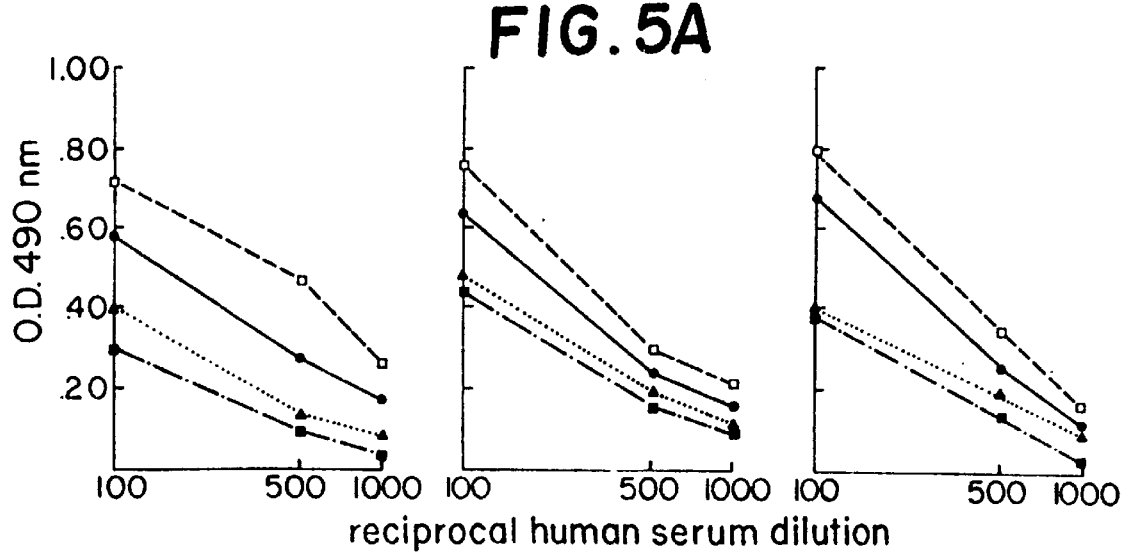
Figure 5B:
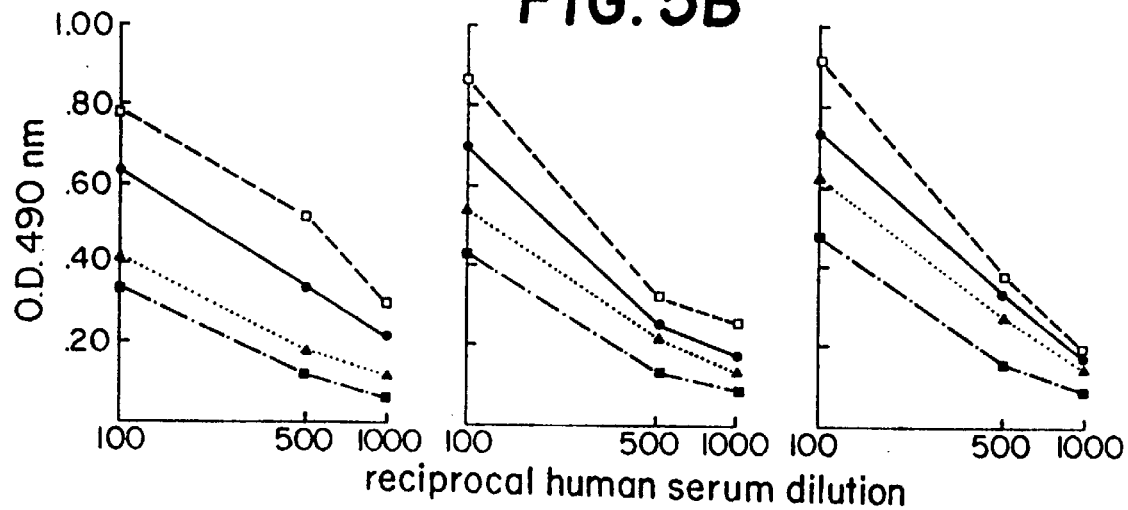
Figure 5C:
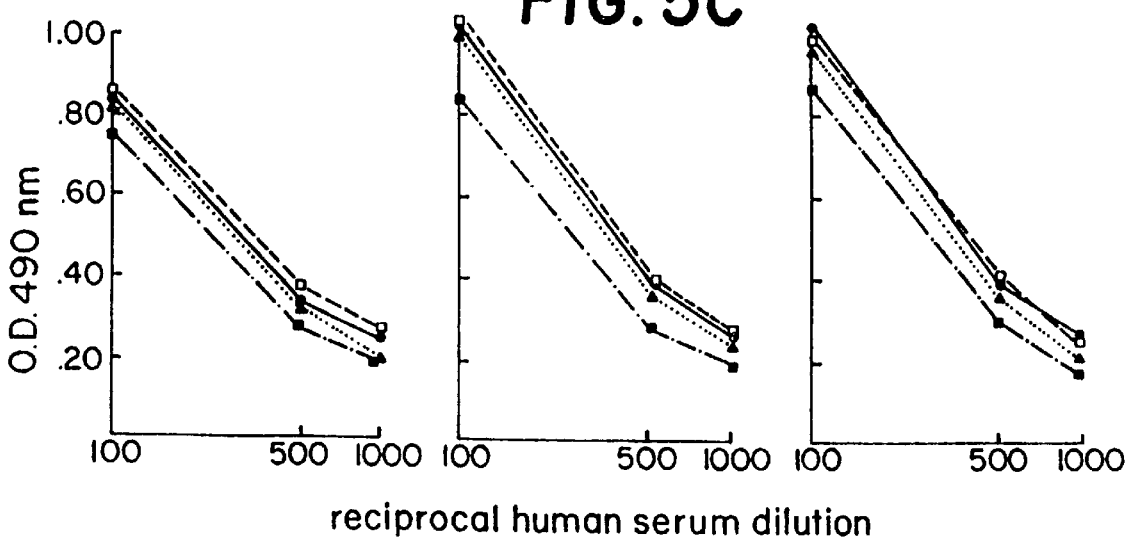

FIG. 5. Reactivity of human serum IgM with (A) P1, (B) P2, (C) polyarginine at 2 μg/ml —.—.—.—.; 5 μg/ml ........; 10 μg/ml ——; 20 μg/ml -------- of each antigen. (Left panels) (pediatric (age 6 months) serum; (middle panels) adult male; (right panels) adult female.

FIG. 6. Competition by HPmAb with human serum IgM reactivity against (A) P1 and (B) P2. The standard ELISA protocol (see Section 6.1.1) was carried out with the following modification: Before the addition of human serum to the antigen-bound wells, 50 μl HPmAb at dilution 1:1,000 ——; 1:10,000 ........,no HPmAb -------- was placed in each well for 1 hour, then washed out and followed by human serum in the noted dilutions; reactivity was detected by use of peroxidase-conjugated anti-human IgM. (A) HPmAb at 1:1,000 dilution blocked ~45% of serum reactivity, at 1:100 and 1:500 dilutions of serum, with P1. (B) HPmAb at 1:1,000 dilution blocked ~25% of serum reactivity with P2 when the serum was diluted 1:100 and ~45% of reactivity when the serum was diluted 1:500.

Figure 7A:
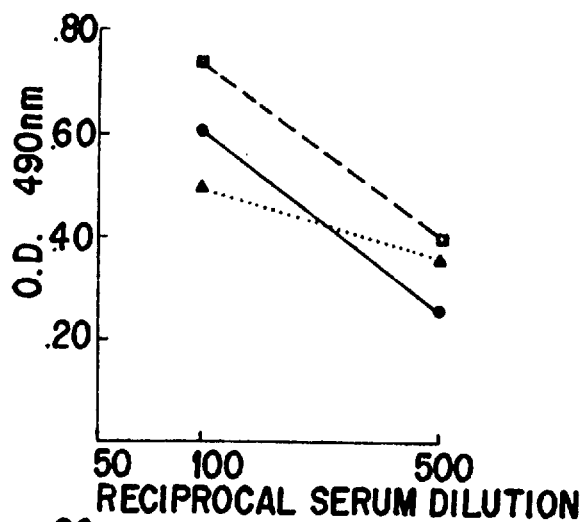
Figure 7B:
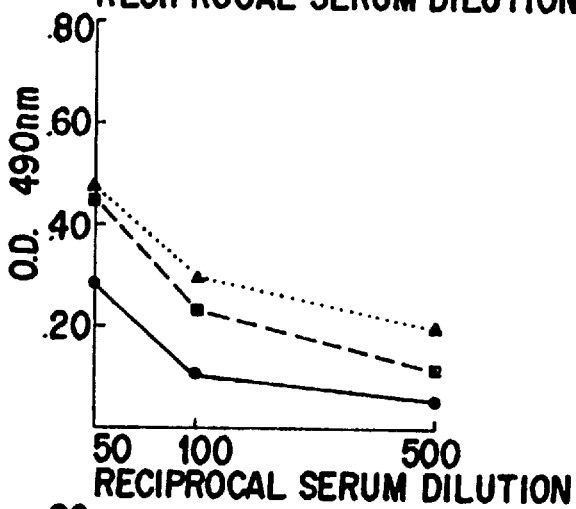
Figure 7C:
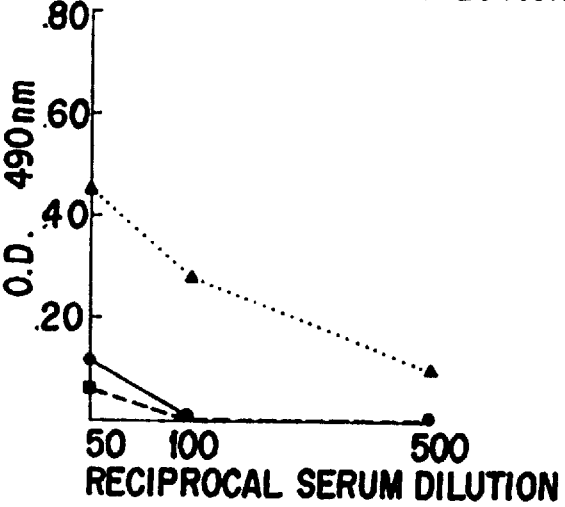

FIG. 7. Reactivity of human serum IgM with P1 ——; P2 --------, and sperm head membrane proteins ........ after absorption of serum on pooled protamines. (A) Nonabsorbed serum; (B) serum absorbed on 100 μg of protamines; (C) serum absorbed on 200 μg of protamines.

Figure 8A:
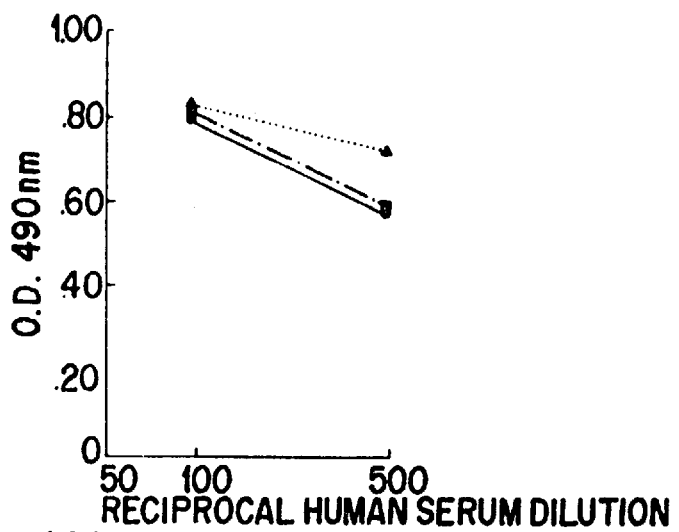
Figure 8B:
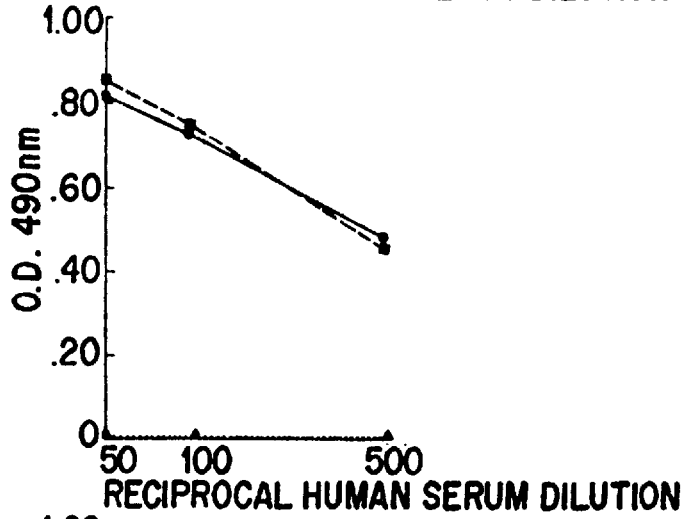
Figure 8C:
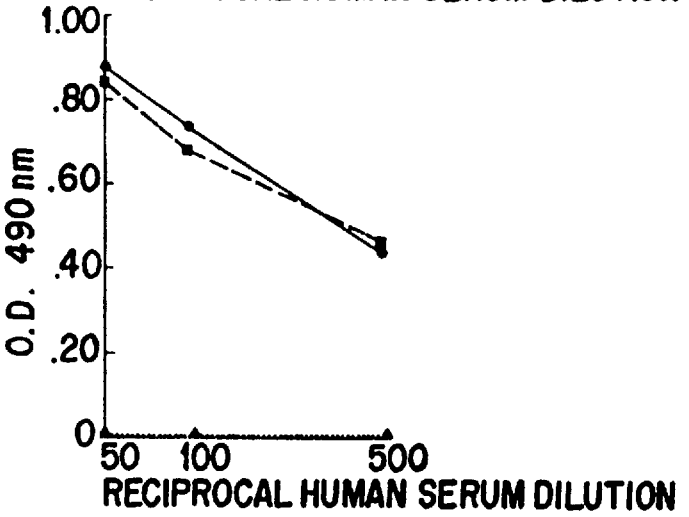

FIG. 8. Reactivity of human serum IgM with P1 —.—.—.—., P2 ——, purified calf thymus histones (including equimolar weights of H1, H2a, H2b, H3, and H4) ........, after absorption on histones. (A) Nonabsorbed serum, (B) absorbed on 200 μg of histones, (C) absorbed on 500 μg of histones.

Figure 9A:
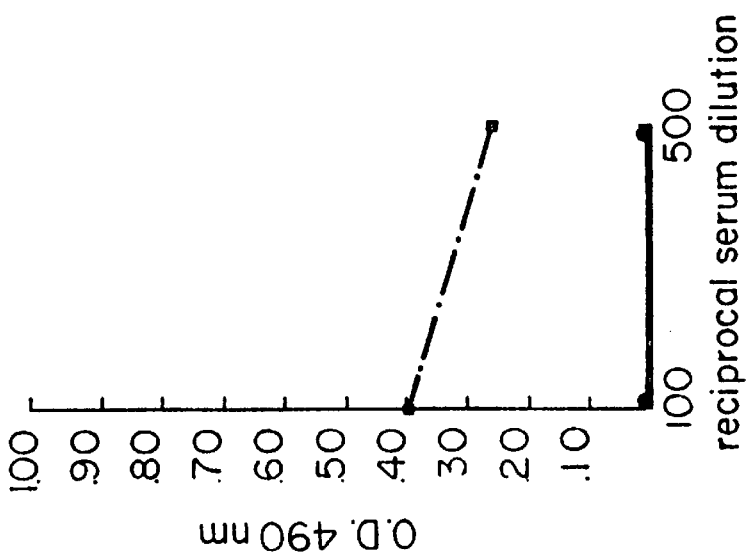

FIG. 9. Reactivity of human serum IgM with P1 ——, P2 --------, polyarginine ........, and polylysine —.—.—.—. (A) Non-absorbed serum; (B) serum absorbed on 200 μg polylysine; (C) serum absorbed on 200 μg polyarginine.

Figure 10A:
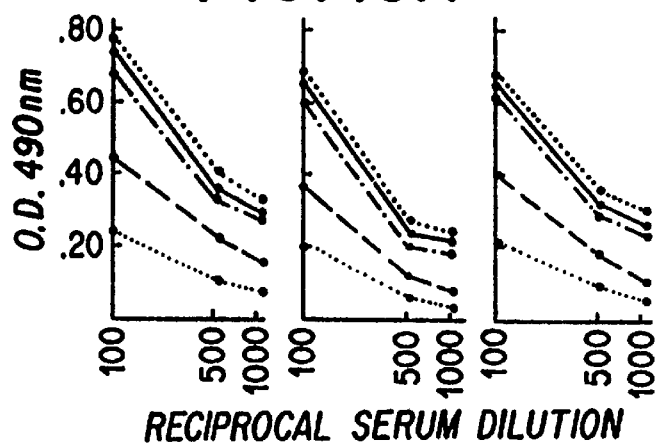

FIG. 10A. The results are shown of an ELISA (O.D. 490 nm) in serum (Rodman, T. C., et al., 1986, J. Immunol. Meth. 94:105–111; Pruslin, F. H., et al., 1986, J. Immunol. Meth. 94:99–103) from each of 3 normal (no clinical findings, HIV negative) adult subjects, to detect antibodies reactive with the following ascending concentrations of protamine-2 (P2): 2 μg/ml ........, 5 μg/ml — — — —, 10 μg/ml —.—.—.—., 20 μg/ml ——, 50 μg/ml --------. The sharp rise in the curve between serum dilutions 1:100 and 1:500 with the higher antigen concentrations suggests that there are two subpopulations of protamine-reactive IgM antibodies in these sera.

Figure 10B:
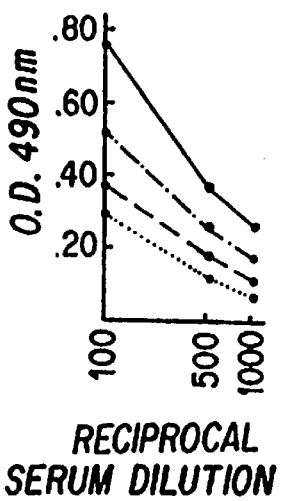

FIG. 10B. Summary curves for assays of IgM of 20 normal adult sera carried out with P2 as antigen at the following concentrations: 2 μg/ml ........, 5 μg/ml — — — —, 10 μg/ml —.—.—.—., 20 μg/ml ——, showing that the rise of the curve at high antigen concentrations, suggestive of a secondary subpopulation of protamine-reactive IgM antibodies, is a prevailing characteristic of sera of normal adults.

Figure 10C:
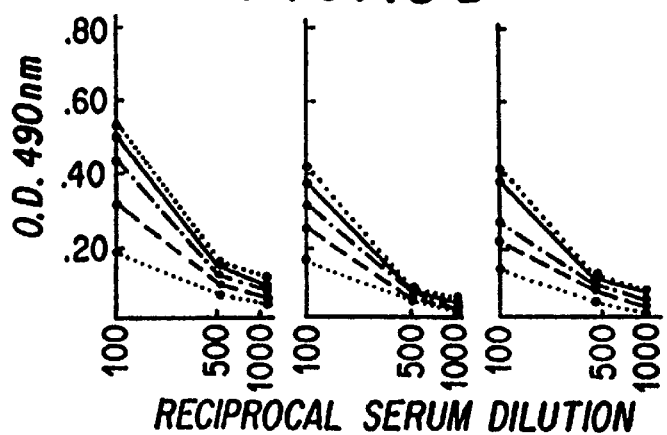

FIG. 10C. Reactivity of same sera as in FIG. 10A with a synthetic decapeptide (DP) that includes the defined antigenic site of protamine, at the same concentrations as in FIG. 10A.

| P2b* | G | Q | S | H | Y | R | R | H | C | S | R | R | R | L | H | R | I | H | R | R | Q | H | R | S | [C |
| | R | R | R | K | R | R | S | C | R] | H | R | R | R | H | R | R | G | C | R | T | R | K | R | T | C | R |
| | R | H | | | | | | | | | | | | | | | | | | | | | | | |
| DP | C | R | R | R | K | R | R | S | C | R | | | | | | | | | | | | | | | |

*McKay, D. J., et al., 1986, Eur. J. Biochem. 156: 5–8)

As for P2 (FIG. 10A), the curves for the higher concentrations of DP show a rise between serum dilutions 1:100 and 1:500, indicating that the secondary population of protamine-reactive IgM antibodies, revealed at high antigen concentrations, is not one with antigen recognition specificity different from that of the primary population, but is one with lower binding affinity.

Figure 10D:
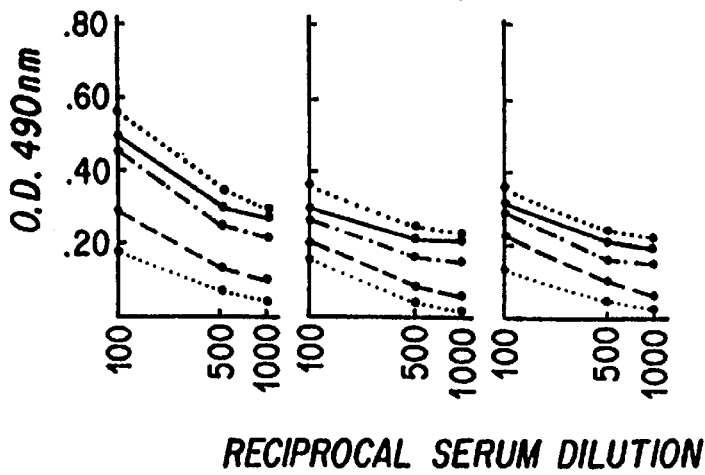

FIG. 10D. IgM reactivity of the same sera as in FIGS. 10A and 10C with the same concentrations of P2b as in FIG. 10A where, however, the diluent was 0.3M NaCl (in contrast to all other assays in which the serum diluent, PBS, was 0.15M NaCl). At increased NaCl molarity, the sharp rise in the curves for high antigen concentrations demonstrated in FIG. 10A was abolished, suggesting that the phase of antigen-antibody binding due to ionic interaction was inhibited. Ionic interaction thus appears to be a major component of the binding of the low affinity subset of protamine-reactive IgM antibodies and, thus, the reactivity of that population was preferentially suppressed.

Figure 11A:
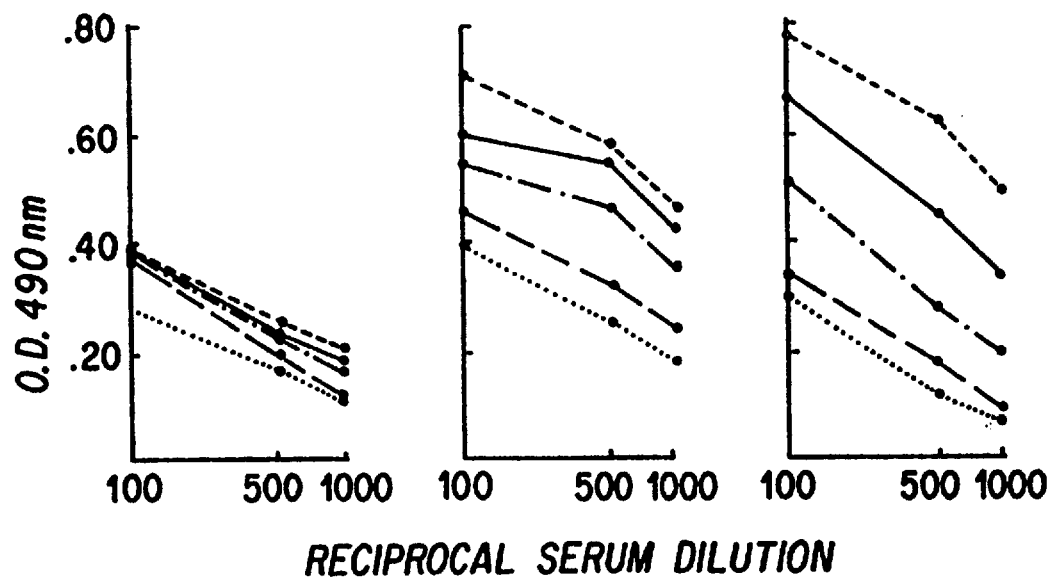

FIG. 11A: Reactivity of IgM antibodies, in serum from each of 3 patients with AIDS, with P2 at ascending concentrations (as described for FIG. 10A). Although, for two of these sera, the total reactivity continues to rise with increasing antigen concentration, the shape of the curves indicates that the increase is that of an antibody population unimodal with respect to affinity rather than that of superimposition of a secondary subpopulation of protamine-reactive IgM antibodies as in FIG. 10A, B, C.

Figure 11B:
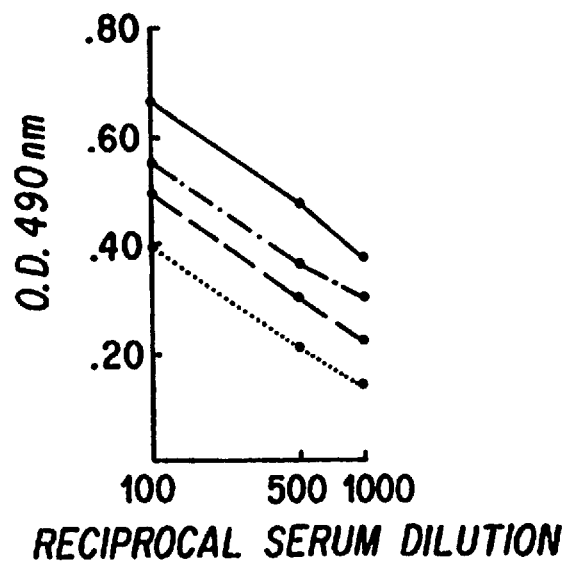

FIG. 11B. Summary curves for assays of 15 sera from AIDS patients for reactivity with P2 (as described supra for FIG. 10B), verifying that absence of the secondary, low affinity, subpopulation of protamine-reactive IgM antibodies is typical of sera from AIDS patients.

Figure 12:
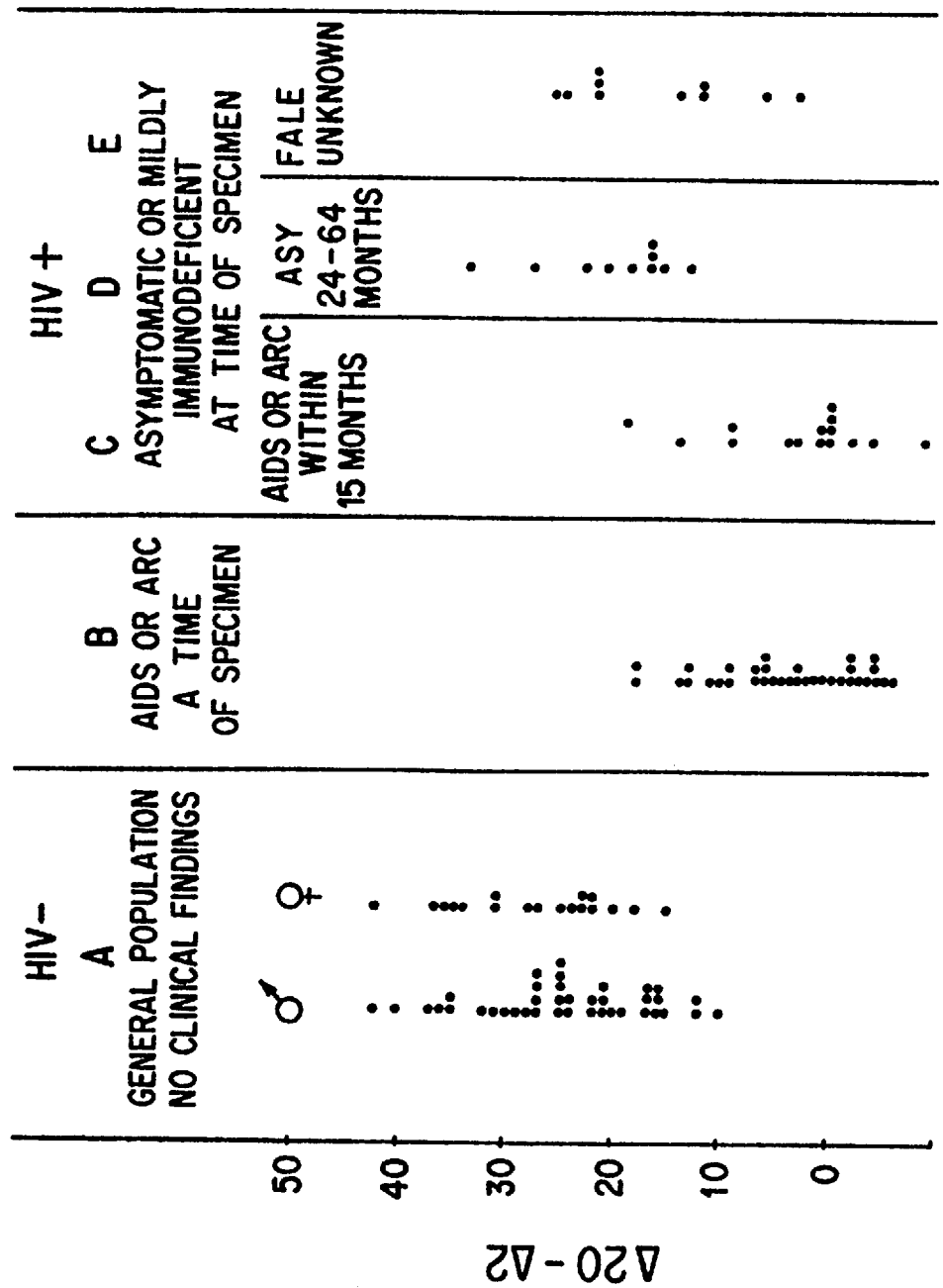

FIG. 12. Distribution of titers of low affinity subset of protamine-reactive IgM antibodies, proportionate to total protamine-reactive IgM, in sera from normal, AIDS and risk-for-AIDS subjects, calculated as $\Delta 20-\Delta 2$, a value obtained by assaying each serum for IgM reactivity with P2 at 2 $\mu$g/ml and 20 $\mu$g/ml, and computing the titer as described infra in Section 7.2. For group D, the documented time intervals from blood sampling to second diagnosis were, from top down, 32, 24, 44, 64, 48, 60, 55, 29, 32, 24 months. The time intervals reflect the time of the last clinical examination of the subjects and thus, are a statement of minimum latency period. All sera were tested for presence of HIV antibodies by western blot using nitrocellulose transfers of electropherograms of HIV proteins: P18, P24, P31, GP41, P51, P55, P65, GP110/120, GP160 (Epitope, Inc. Beaverton, Oreg.). Serum was designated positive when two or more bands were stained, and negative when no bands were stained.

Figure 13A:
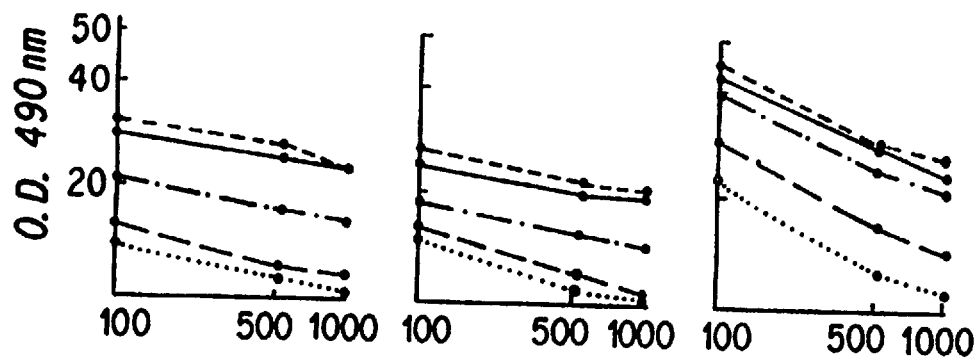
Figure 13B:
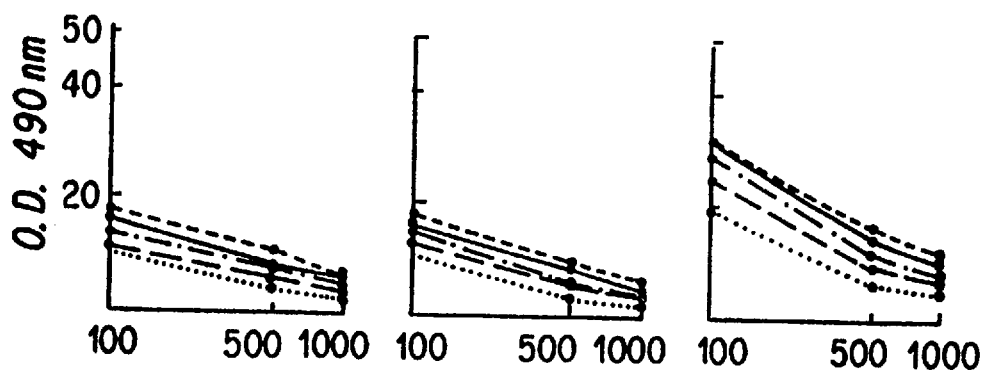

FIG. 13. Reactivity of IgM in serum of each of 3 pediatric subjects (with ages of 28 days, 12 days, 5 months, no clinical findings) with (A) P2 and (B) DP at ascending concentrations (as described for FIGS. 1A and 1C). The similarity in the curves for P2 and DP confirm the identity of the antigenic site. The shapes of the curves indicate that pediatric serum IgM antibodies reactive with that site are homogenous or unimodal with respect to affinity.

5. DETAILED DESCRIPTION OF THE INVENTION

The present invention is directed to protamine-reactive IgM antibodies, and their prognostic, diagnostic, and therapeutic uses. In particular, the invention relates to low-affinity binding, protamine-reactive serum IgM antibodies, which recognize an epitope characterized by an arginyl cluster. The detection and/or measurement of such protamine-reactive antibodies in human sera can be used in diagnostic assays to predict the period of latency between HIV seropositivity and progression to clinical manifestations of AIDS. The invention also provides methods and kits for detection and/or measurement of low affinity binding, protamine-reactive IgM antibodies for prognosis and/or diagnosis of AIDS and other disorders.

5.1. Protamine-Reactive IgM Antibodies

The present invention relates to protamine-reactive IgM antibodies. Such antibodies can recognize an epitope of protamine characterized by an arginyl cluster, in particular, four arginyl residues, including a triplet, within a six amino acid residue piece. In one embodiment, such an arginyl cluster epitope is that of a linear sequence. In another embodiment, the epitope can be conformationally dependent, resulting from a configuration which produces an antigenic determinant comprising four arginyl residues, including a triplet cluster. In a particular embodiment, the IgM antibodies bind with low affinity to the arginyl cluster epitope.

In a specific embodiment, the invention relates to protamine-reactive IgM antibodies which are natural antibodies (i.e., not induced) present in normal human sera.

As detailed in Section 6, infra, we have established that the sera of all clinically normal people over 12 days of age contain IgM antibodies reactive with protamines, that those antibodies are a definitive set of the circulating IgM with a high order of specificity, and have defined the antigenic site with which those antibodies are reactive.

As described infra, the protamine-reactive IgM antibodies of the invention are detectable in significant titer in virtually all sera of normal adult males and females and of normal pediatrics (aged 7 days to 2 years). Commonality between the protamine-reactive IgM antibodies of pediatric and adult sera was established by the demonstration of similarity in antigen recognition and reaction equilibria. The protamine-reactive IgM antibodies found in the sera of pediatrics cannot be attributed to immunogenic stimulation by protamine since protamines are synthesized de novo in the post-puberal testis and are incorporated into the nuclei of no cells other than those of the spermiogenic series. Nor may the protamine-reactive IgM antibodies in sera of neonates be attributed to maternal origin since IgM does not cross the placenta. There is, therefore, sound basis for inferring that human sera contain a subset of "natural" antibodies reactive with, but not induced by, protamines.

Protamines are sequestered from the immune system during their synthesis and cellular incorporation (Dym, M. and Fawcett, D. W., 1970, Biol. Reprod. 3:308–326) and we have shown that protamines are non-immunosuppressive, i.e., they do not inhibit T-cell mitogenesis in vitro as do other sperm-derived proteins (Rodman, T. C., et al., 1985, Science 228:1211–1215). Therefore, the sera of post-puberal males and sexually experienced females may contain some protamine-reactive antibodies that may be attributable to immunogenic induction by protamines. Thus, we postulate that the protamine-reactive IgM antibodies of adult human sera includes two subsets differing in origin: (1) natural antibodies, and (2) induced antibodies.

The principle characteristic of the antigenic site recognized by the protamine-reactive serum IgM antibodies is that of clustered arginyl residues with an apparent minimum requirement of four arginyl residues, including a triplet, within a six residue piece; the binding reaction is not dependent upon charge attraction. As shown by a series of immunoabsorption procedures (see Section 6, infra) the protamine-reactive serum IgM antibodies are a discrete set with a high order of specificity.

The antibody molecules of the invention are protamine-reactive IgM antibodies, including fragments thereof which contain the idiotypic region of the antibody molecules; these include but are not limited to the fragments which include the Fv region, such as the Fab, the F(ab')$_2$, Fab' fragments and the like. Antibody fragments which contain the idiotype of the molecule could be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')₂ fragment, and the Fab fragments which can be generated by treating the antibody molecule with papain and a reducing agent.

5.2. Use in Prognostics and Diagnostics: Prediction of Latency From HIV Infection to Manifestation of AIDS As detailed in Section 7, infra, the measurement of serum anti-protamine IgM antibodies provides a reliable prognostic indicator of the period of latency between HIV infection and the onset of manifestations of AIDS. The presence or absence in serum of a low-affinity subset of the protamine-reactive IgM antibodies of the invention is indicative of the capacity of an HIV-infected individual to withstand the pathogenetic progression to AIDS. The characteristic property of the subset of anti-protamine IgM antibodies whose absence from serum correlates with a relatively short period of HIV latency is the low binding affinity to protamine relative to other IgM anti-protamine antibodies present in adult sera. These low affinity anti-protamine IgM antibodies are reactive with an epitope characterized by an arginyl cluster, in particular, four arginyl residues, including a triplet, within a six amino acid residue piece. Such low-affinity anti-protamine antibodies may be natural antibodies.

The low affinity subset of serum protamine-reactive IgM antibodies may be assayed for prognosis of AIDS. Such antibodies are detectable in sera of normal subjects and HIV-infected individuals who subsequently exhibit a significant period of latency, but are absent or deficient in sera of individuals diagnosed with AIDS and sera of HIV infected individuals who, though asymptomatic at the time of the sampling, proceed to AIDS within a relatively short time. Thus, quantitative determination of the absence or deficiency of such antibodies in HIV-seropositive individuals can be relied on as an indication of relatively imminent onset of AIDS.

The quantitative determination and/or detection of low-affinity anti-protamine serum IgM can also be used to monitor the efficacy of therapeutic treatments, to assist in selection of appropriate subjects for clinical trials, and to provide an additional modality for diagnosis of AIDS or ARC. It is also envisioned that the detection and/or measurement of these anti-protamine antibodies may be used similarly in the prognosis and diagnosis of other immune abonormalities.

The various assays and methods for detection and quantitative determination which can be used are described infra.

5.3. Assays of Serum Protamine-Reactive IgM Antibodies

In a particular embodiment of the invention in which the assay is for prognosis and diagnosis of AIDS, the presence of a low-affinity subset of protamine-reactive IgM serum antibodies can be assayed by any of the methods described infra. As one example, a low-affinity subpopulation of anti-protamine IgM antibodies can be identified by allowing a fixed volume of the antibody mixture (e.g., serum) to react with increasing amount of antigen. As concentration of antigen increases, high affinity antibodies are saturated and antibodies of lower affinity will react with antigen. In a preferred embodiment, the ELISA described in Section 5.3.3 infra and in Section 7 infra can be used.

5.3.1. Assay Systems

Any assay system known in the art may be used for quantitative determination and/or detection of the anti-protamine IgM antibodies (or antigen binding region thereof) of the invention. For example, such assays include but are not limited to the following immunoassays, including competitive and noncompetitive assay systems: radioimmunoassays, ELISA (enzyme linked immunosorbent assay), "sandwich" immunoassays, precipitin reactions, gel diffusion precipitin reactions, immunodiffusion assays, agglutination assays, complement-fixation assays, immunoradiometric assays, fluorescent immunoassays, protein A immunoassays, and immunoelectrophoresis assays, to name but a few.

5.3.2. Antigens

The antigens which can be used in assay systems for the quantitation of protamine-reactive IgM antibodies include any antigen comprising an arginyl cluster, in particular, a sequence comprising four arginyl residues, including a triplet, within a six amino acid residue piece, or an epitope that is immunologically cross-reactive with the foregoing. In one embodiment, such an arginyl cluster epitope is that of a linear sequence. In another embodiment, the epitope can be conformationally dependent, resulting from a configuration which produces an antigenic determinant comprising four arginyl residues, including a triplet cluster. In a specific embodiment, a peptide comprising four arginyl residues, including a triplet, within a six amino acid piece, can be used as the antigen.

Thus, peptides which can be used as antigen include but are not limited to those which comprise the following sequences:

| R | R | R | R | R | R |            |
|---|---|---|---|---|---|------------|
| X | R | R | R | R | X |            |
| R | R | R | R | R | X | or inverse |
| R | R | R | R | X | R | "          |
| R | R | R | X | R | R | "          |
| R | R | R | R | X | X | "          |
| R | R | R | X | R | X | "          |
| R | R | R | X | X | R | "          |
| X | R | R | R | X | R | "          | where R=arginine and X=any other amino acid. Other antigens which can be used include but are not limited to those listed in Table VII, infra (see Section 6.2.5) namely those proteins containing a sequence of four arginyl residues, including a triplet, within a six amino acid sequence. In addition, any protamine can be used as the antigen, e.g., human protamine 1 (P1), human protamine 2 (P2). The protamines are most satisfactory as antigens when their extraction and purification procedure includes a step to block the cysteinyl residues from forming disulfide cross-linkages. That blocking may be effected by any of the known methods, e.g., aminoethylation, s-methylation and iodoacetylation. In addition, the protamines may be used as antigens in the method of this invention even though they have not been treated to inhibit disulfide cross-linking between cysteinyl residues.

Other antigens which can be used in the immunoassays of the invention can be identified by their ability to be bound by anti-protamine monoclonal antibody HPmAb (ATCC Accession No. HB 9668), which recognizes an epitope similar or identical to that of the protamine-reactive IgM antibodies of the invention.

5.3.3. Assay Method for Prediction of HIV Latency Period

The assay and computation method described herein provides a modality for predicting the likely period of HIV latency before onset of AIDS, for an infected individual.

Such information may be useful in the medical management of individual patients, in projection of community needs for medical care facilities, and in the selection of appropriate subjects for trial of proposed therapeutic agents. It also provides additional criteria for AIDS' diagnosis.

The assay and method described herein are but one example of the derivation of a quantitative index for use in AIDS' prognosis; other such examples, and modifications of the procedure herein described, are also envisioned and are within the scope of the invention.

An enzyme-linked immunosorbent assay (ELISA) which can detect low-affinity binding, protamine-reactive serum IgM antibodies can be carried out. The ELISA is performed as described in Section 7 infra (see also the description of FIG. 10A, Section 4, supra), with ascending concentrations of antigen (e.g., protamine 2) at 2, 5, 10, 20, and 50 µg/ml. Briefly, the test procedure is comprised of the following steps:

(i) Antigen coating:

Assay wells of a microtiter plate are coated with antigen (50 µl preferred), by addition of antigen solution to wells, followed by a 4 hour incubation. With protamine 2 as antigen, the preferred antigen concentrations for use are 2 µg/ml and 20 µg/ml.

(ii) Blocking:

Antigen solution is washed out with buffer and all wells are filled to the brim with blocking solution to coat regions not coated with antigen, thereby inhibiting non-specific binding to the well surface in subsequent steps.

(iii) Binding of serum antibodies:

Blocking solution is washed out and diluted serum (50 µl preferred) is added to each well. Each specimen serum is tested in triplicate at each of the two dilutions. We have found serum dilutions 1:100 and 1:500 to be suitable when protamine 2 is used as antigen and, for most human sera, to have low enough serum background values for valid interpretation of test results to be made. However, with various peptides bearing the antigenic site, other pairs of serum dilutions varying from undiluted serum to 1:1000 dilution, have been found useful.

(iv) Detection of bound IgM antibodies:

After 3 hours, serum dilutions are washed out and 50 µl of peroxidase-labeled second antibody (anti-human IgM) is added to each well. After 1.5 hours, the second antibody is washed out, and 50 µl of peroxidase substrate is added. After 30 minutes, 50 µl of 2.5N sulfuric acid is added to each well to stop the action of enzyme (peroxidase) on substrate, thus terminating production of chromatic product.

(v) Measurement:

The plate is placed in an automatic plate reader which moves the plate to center each well over a beam of filtered light so that the optical density (O.D.) of the incident light (e.g., 490 nm) is read for each well and recorded.

(vi) Computation:

Optical density at 490 nm ($O.D._{490}$) (Y axis) is then plotted against reciprocal serum dilution (X axis) (see e.g., FIGS. 10, 11 infra). An increase in slope of the reactivity curve at high antigen concentration (see FIG. 10A) is indicative of the presence of a secondary (low affinity) subset of protamine-reactive IgM antibodies. This increase is not seen in assays of sera from patients diagnosed with AIDS (see FIG. 11A). Thus, the observed absence of the increase in slope of the reactivity curve at high antigen concentration, representative of a low affinity subset of anti-protamine IgM antibodies, can provide an additional modality for diagnosis of AIDS or ARC.

A system of computation can be devised to quantitate this low affinity subset of protamine-reactive IgM antibodies, i.e., to assess the proportionate titer of the secondary subset of protamine-reactive IgM antibodies represented by the increase in slope of the reactivity curve with high antigen concentration, as follows: 2 µg/ml and 20 µg/ml are empirically selected as suitable test antigen concentrations. The rise of the curve between two points on the X axis, serum dilutions 1:100 (x1) and 1:500 (x2), may be expressed as the difference between the O.D. values on the Y axis for those two points. The increase in rise from that of the 2 µg antigen (protamine) curve to that of the 20 µg curve is (O.D.x1–O.D.x2) at 20 µg/ml antigen minus (O.D.x1–O.D.x2) at 2 µg/ml antigen, and may be noted as Δ20–Δ2.

Values for Δ20–Δ2 are then computed. A value of "15" can be considered to be the lower limit of "normal" range (see Section 7.2, infra). A value within the normal range for an HIV-seropositive serum is predictive of a latency period of at least two years before the manifestation of AIDS, and probably longer, while a low Δ20–Δ2 value is predictive that progression to the disease is imminent.

It should be noted that, as the method has been applied to other peptides bearing the designated antigenic site (see Section 5.3.2) it has been found that, while optimum results are always obtained when the ratio of the two concentrations of the antigen is 1:10, good results are also obtainable with other pairs of concentrations using the various alternate peptides bearing the designated antigenic site.

It should also be noted that various body fluids of a patient may be used as an assay sample, e.g., serum, plasma, with serum preferred for use.

5.4. Therapy

The low-affinity, protamine-reactive IgM antibodies of the invention have potential use in therapy of AIDS and other immune abnormalities. It is envisioned that the low-affinity anti-protamine antibodies may have a role in protecting an HIV-infected individual against the onset of AIDS. The antibodies may have similar protective effects in individuals afflicted with, or with a predisposition for, other conditions of immune abnormality. Thus, it is envisioned that the antibodies of the invention can confer short term protection to a host by passive immunotherapy, i.e., by the administration of such pre-formed low-affinity anti-protamine IgM. Human immunoglobulin is preferred for such use because a heterologous immunoglobulin will provoke an immune response to its foreign immunogenic components. In one embodiment, the low affinity subset of protamine-reactive IgM antibodies of the invention may be isolated from pooled human sera in adequate quantities for use in passive immunotherapy, to defer the progression to AIDS in HIV-positive individuals.

A molecular clone relating to the low affinity protamine-reactive antibodies of the invention can be prepared by known techniques. Recombinant DNA methodology (see e.g., Maniatis, T., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof, with properties similar to those of the low affinity protamine-reactive antibodies.

A murine monoclonal antibody molecule may also be valuable for use in passive immunotherapy, by construction of so-called "chimeric antibody" molecules. Chimeric antibody molecules may be prepared containing a mouse antigen-binding domain with human constant regions (Morrison et al., 1984, Proc. Natl. Acad. Sci. U.S.A. 81:6851; Takeda et al., 1985, Nature 314:452).

Antibodies may be purified by known techniques, e.g., immunoabsorption or immunoaffinity chromatography, chromatographic methods such as HPLC (high performance liquid chromatography), or a combination thereof, etc.

5.5. Diagnostic Kits

The invention also encompasses diagnostic kits for carrying out the methods disclosed above. In one embodiment, the diagnostic kit comprises (a) a peptide or protein comprising a sequence of four arginyl residues, including a triplet, within a six amino acid residue sequence (an "arginyl cluster"); and (b) a conjugate of a specific binding partner for IgM antibodies and a label capable of producing a detectable signal. In other embodiments, the diagnostic kit can comprise (a) a peptide or protein comprising a conformationally-dependent epitope, which epitope comprises four arginyl residues, including a triplet cluster, and (b) a conjugate as above. In yet another embodiment, the kit can comprise (a) a peptide or protein characterized by the ability to be bound by HPmAb, and (b) a conjugate as above. The reagents may also include ancillary agents such as buffering agents and protein stabilizing agents, e.g., polysaccharides and the like. The diagnostic kit may further comprise, where necessary, other components of the signal-producing system including agents for reducing background interference, control reagents, an apparatus for conducting a test, etc.

In another embodiment, the diagnostic kit comprises a conjugate of an antibody reactive with a peptide or protein comprising a sequence of four arginyl residues, including a triplet, within a six amino acid residue sequence, and a label capable of producing a detectable signal. In other embodiments, a conjugate of a label and an antibody reactive with a peptide or protein comprising a conformationally-dependent arginyl cluster epitope, or a peptide or protein characterized by recognition by HPmAb, may be used. Ancillary agents as mentioned above may also be present.

In a preferred embodiment, an ELISA kit is used, comprising a sequence of four arginyl residues, including a triplet, within a six amino acid residue sequence, immobilized on a solid support, and a conjugate of a specific binding partner for IgM antibodies and a label capable of producing a detectable signal which is an enzyme such as horseradish peroxidase.

6. EXAMPLE: PROTAMINE-REACTIVE NATURAL

IgM ANTIBODIES IN HUMAN SERA

In the examples detailed herein, we describe the identification of a set of natural IgM antibodies in human serum that are reactive with protamines, a class of low molecular weight basic nucleoproteins that are synthesized de novo in the postpuberal testis and are unique to sperm. Those antibodies were detected by ELISA in significant titer in all of 100 sera of normal adult males and females and in 26 of 28 sera of normal pediatrics aged 7 days to 2 years. Commonality between the protamine-reactive IgM antibodies of pediatric and adult sera was established by the demonstration of similarity in antigen recognition and reaction kinetics. Therefore, the role of protamines as either immunogenic stimulus or antigenic target of that set of natural antibodies is not likely.

The antigenic site recognized by the protein-reactive serum IgM antibodies was characterized by comparison with the pattern of antigen recognition by a monoclonal antibody to human sperm protamines (HPmAb). By the use of synthetic peptides simulating the amino acid sequences of various segments of human protamine 2 and of polyarginine, polylysine, and histones as test antigens, the principle characteristic of the antigenic site recognized by both HPmAb and the serum IgM antibodies appeared to be that of clustered arginyl residues with an apparent minimum requirement of four arginyl residues, including a triplet, within a six residue piece; for both, the reaction was shown to be not dependent upon charge attraction. A series of immunoabsorption procedures indicated that the protamine-reactive serum IgM antibodies are a discrete set with a high order of specificity.

A search of protein databases revealed that the putative minimum epitope is present in four or five human autogenous proteins, all moieties of the immune system, and in a number of viral proteins (Table VII).

6.1. Materials and Methods

6.1.1. Enzyme-Linked Immunosorbent Assay for Serum Antibodies

The enzyme-linked immunosorbent assay (ELISA) method by which the data of Table I (infra) were assembled and which were used throughout this study has been described (Pruslin, F. H., et al., 1986, J. Immunol. Methods 94:99; Rodman, T. C., et al., 1986, J. Immunol. Methods 94:105). Briefly, 50 $\mu$l of antigen (specified concentration) was placed in each well of a 96-well flat-bottomed microtiter plate, covered, and held at room temperature for 4 hours. The wells were washed 20 times with 0.01% TWEEN-20 in phosphate-buffered saline (PBS), then filled to the rim with 5% bovine serum albumin (BSA) in PBS, covered and held at 5° C. overnight. The plates were brought to room temperature and washed 20 times and 50 $\mu$l of serum or monoclonal antibody (mAb) (diluted with 1% BSA) was added to each well. After 2 hours at room temperature, the wells were washed 20 times, and 50 $\mu$l of peroxidase-conjugated second antibody [goat F(ab')$_2$ anti-human IgM $\mu$ chain specific, or goat F(ab')$_2$ anti-mouse IgA, IgG, and IgM] was added. The plates were covered, held at room temperature for 1.5 hours, and washed 20 times. Fifty $\mu$l of substrate (ortho-phenylenediamine) was added to each well and, after 30 minutes, the reaction was stopped by the addition of 50 $\mu$l of H$_2$SO$_4$ (2.5N). The optical density of the colored solution in each well was read at 490 nm in an automated plate reader. That protocol was developed to maximize sensitivity and to minimize ambiguity arising from serum background and plate-to-plate differences in binding efficiency (Rodman, T. C., et al., 1986, J. Immunol. Methods 94:105).

6.1.2. Antigens

Purified protamine 1 (P1) and protamine 2 (P2) were prepared as described (Rodman, T. C., et al., 1982, J. Cell Sci. 53:227) with modifications. Briefly, spermatozoa were isolated from pooled ejaculates and sonicated to separate heads from tails. The heads were collected and, by treatment with an ionic detergent such as TRITON X-100®, were separated into a membrane protein fraction and a DNA-nucleoprotein fraction. The latter was solubilized in 4M guanidinium chloride (GuCl), 1% 2-mercaptoethanol, and treated with ethylene-imine to aminoethylate the cysteinyl residues of the protamines, thereby preventing formation of disulfide bonds, then dialyzed against 50 mM HCl and chromatographed on a BIOREX 70 resin column with stepwise elution by ascending concentrations of GuCl. Pure P1 appears in the 23% eluate, Pure P2 (a and b) appears in the 27% eluate, while a series of phosphorylated variants of P2 together with a portion of the P1 appear in an intermediate pool (25% eluate). The P1 and P2 (23 and 27% eluates) were each dialyzed overnight against 50 mM HCl, followed by a 2–3 hour dialysis against PBS, pH 7.2, and the concentration of each was measured by a dye-binding assay (Bradford, M. M., 1976, Anal. Biochem. 72:248). The synthetic peptides were prepared by the method of Merrifield (Merrifield, R. B., 1963, J. Am. Chem. Soc. 85:2149) and purified by reverse-phase HPLC (high-performance liquid chromatography).

Polyarginine (10,000–20,000 daltons molecular weight) was obtained from Chemical Dynamics Corp. (Plainfield, NJ) and polylysine (15,000–30,000 daltons molecular weight) was from Sigma Chemical Co. (St. Louis, Mo.).

6.1.3. Monoclonal Antibodies

The mAb to human sperm protamines (HPmAb) was obtained by immunization of a BALB/c mouse with the nuclear protein fraction of human sperm, and fusion of the spleen cells with a nonsecreting mouse myeloma. In preparation for the study herein described, the hybridoma culture was recloned by limiting dilution to assure monoclonality. The HPmAb was isolated from ascites fluid by ammonium sulfate precipitation and purified by dialysis against PBS followed by DEAE (diethyl aminoethyl; ion-exchange) column chromatography.

The mAb against chick myosin, used as control, was similarly prepared from ascites fluid.

6.1.4. Human Sera

The normal human sera were either donated by laboratory personnel or obtained as clinical specimens identified only with regard to date of birth, sex, and "no findings."

6.1.5. Immunoabsorptions

For each of the immunoabsorption procedures, the weight of absorbing protein stated in the description of the figure (Section 4, supra) was coupled to 0.5 gm cyanogen bromide-activated a molecular sieve column, such as SEPHROSE® 4B (Pharmacia Fine Chemicals, Piscataway, N.J.) in an 0.7×10 cm column. Forty to fifty μl serum, diluted 1:50 with 1% BSA/sodium borate buffer, pH 7.5, was layered on the column, which was then mixed end over end, overnight at 4° C. The absorbed serum was drained out of the column and tested by ELISA at the noted dilutions for reactivity with the designated antigens.

6.1.6. Homology Search

A search for proteins bearing a six residue segment designated as one with a minimum of four arginyl residues including a cluster of three was carried out by the Protein Identification Source of the National Biomedical Research Foundation, and augmented by our own survey of the current literature.

6.2. Results

6.2.1. Protamine-Reactive Antibodies Occur in Human Sera

The data of Table I show that protamine-reactive antibodies are present in all sera of a cohort of normal subjects aged 0–60 years.

TABLE I

OCCURRENCE OF HUMAN SERUM ANTIBODIES REACTIVE WITH HUMAN SPERM PROTAMINES*

| Age | Number Tested | IgM | IgG |
|---|---|---|---|
| 0 (cord blood) | 1 | 0 | 1 |
| 1 day | 2 | 0 | 2 |
| 2 days | 2 | 0 | 2 |
| 4 days | 3 | 0 | 3 |
| 5 days | 2 | 0 | 2 |
| 7 days | 3 | 2 | 3 |
| 10 days | 3 | 2 | 3 |
| 12–28 days | 11 | 11 | 11 |
| 1–12 months | 9 | 9 | 9 |
| 1–2 years | 4 | 4 | 4 |
| adult male | 41 | 41 | 41 |
| adult female | 59 | 59 | 59 |

*All sera were assayed at 1:100, 1:500, 1:1,000 dilutions with pooled human protamines as antigen. All sera designated as positive displayed reactivity at 1:500 dilution. Titers of IgM and IgG reactivity with protamines were computed relative to that of a reference serum (Pruslin, F. H., et al., 1986, J. Immunol. Methods 94:99; Rodman, T. C., et al., 1986, J. Immunol. Methods 94:105). Negative IgM values were <1% of reference serum; positive IgM values for pediatric sera ranged from 15% (7-day neonate) to 65% of reference serum; IgG values were 40–90% of reference serum. For adult sera, the range of IgM reactivity with protamine was 54–180% of reference serum and that of IgG reactivity was 50–200%. Total IgG and IgM titers for all sera were within normal range for the respective age groups (de Preval, C., 1982, Immunology, Bach, J. F. and Schwartz, R. S., eds., John Wiley & Sons, New York, p. 230).

As shown in Table I, protamine-reactive IgG antibodies are present in all sera, and IgM antibodies are present in sera of those subjects whose immune systems have matured sufficiently to produce a significant titer of IgM (de Preval, C., 1982, Immunology, Bach, J. F. and Schwartz, R. S., eds., John Wiley & Sons, New York, p. 230). A proportionality of the total IgM represented by the protamine-reactive IgM was computed for each serum of a group from each subject category (FIG. 1). The computation defines the titer of protamine reactive antibody, compared with the titer of total IgM, within a similar assay protocol. The values derived for that proportionality, i.e., ratio of protamine-reactive IgM to total IgM, for all population subgroups falls within a relatively narrow range (FIG. 1), suggesting that the protamine-reactive antibodies represent a specific component of normal human serum.

6.2.2. Identification of Human Sperm Protamines

The nuclear proteins of human sperm include two protamines, designated P1 and P2. Determination of the amino acid sequences has shown that P2 exists as two variants, P2a and P2b, differing only in that P2a has three additional residues at its NH$_2$ terminus (Table IIA) (McKay, D. J., et al., 1986, Eur. J. Biochem. 156:5; Ammer, H., et al., 1986, Biol. Chem. Hoppe-Seyler 367:515).

TABLE II

AMINO ACID SEQUENCES

A. Human sperm protamines

| | |
|---|---|
| P1 | A R Y R C C R S Q S R S R Y Y R Q R Q R S R R R R R R S C Q T R R R A M R C C R |
| P2a | R T H G Q S H Y R R R H C S R R R L H R I H R R Q H R S C R R R K R R S C R H R |
| P2b | G Q S H Y R R R H C S R R R L H R I H R R Q H R S C R R R K R R S C R H R R R H |
| P1, cont. | P R Y R P R C R R H |
| P2a, cont. | R R H R R G C R T R K R T C R R H |
| P2b, cont. | R R G C R T R K R T C R R H |

B. Synthetic peptides (P2b fragments)

| Peptide | Sequence |
|---|---|
| peptide 1 (P2b 16–25) | H R I H R R Q H R S |
| peptide 2 (P2b 26–35) | C R R R K R R S C R |
| peptide 3 (P2b 42–51) | R G C R T R K R T C |

We have recently demonstrated that P1 and P2a,b are obtainable, in purified form and in high yield, separately from a group of phosphorylated variants of P2 (Pruslin, F. H., et al., 1987, Gamete Res. 18:179). Those preparations of P1 and P2 are perferred for use as antigen in solid-phase assay since each is a small molecule with high positive charge favoring linear orientation on the polystyrene surface and there is little possibility of intramolecular crosslinkage since, in the preparative process, the cysteinyl residues are amino-ethylated (see Section 6.1.2), thus blocking formation of disulfide bonds.

6.2.3. Specificity of Anti-Protamine Monoclonal Antibody For Protamines: Definition of the Epitope We have prepared a mAb (HPmAb), using the nucleoprotein fraction of human sperm as the immunogen, that is reactive with P1 and P2 and the phosphorylated variants of P2 and with no other component of human sperm (FIG. 2). Repeated assays, using different batches of purified P1 and P2 have confirmed that, although the reactivity with each is of the same order of magnitude, HPmAb displays greater reactivity with P1 when assayed against molar equivalents of P1 and P2. Inspection of the primary structure of those molecules (Table IIA) reveals that there is not extensive amino acid sequence homology between the two; positional homology at four residues within a six residue piece is displayed in only three segments: amino acids 7–12 of P1 with 20–25 of P2b, 29–34 of P1 with 34–39 of P2b, and 45–50 of P1 with 49–54 of P2b. However, for each, P1 and P2b, arginine residues constitute 48% of the amino acid composition, and, in each, a number of the arginyl residues are clustered. Although a greater proportion of the arginyl residues of P2 is grouped in clusters of two or more residues, P1 has a single cluster of six arginyl residues. Analysis of the amino acid sequences suggested that recognition of the protamines by HPmAb might be dependent upon arginine density. The HPmAb, therefore, was assayed against three synthetic decapeptides (Table IIB) representing segments of P2 selected for differential density of arginine and for variety of other amino acids, and against polyarginine, representing maximum arginine density.

The results are presented in Table III.

TABLE III

REACTIVITY ($OD_{490}$) OF ANTI-PROTAMINE MONOCLONAL ANTIBODY WITH SYNTHETIC PEPTIDES (TABLE II) AND POLYARGININE

| Experiment* | Antigen (µg/ml) | Anti-Protamine mAb (HPmAb) 1:1,000 dilution | Mysoin mAb 1:1,000 dilution | Nonimmunized mouse serum 1:100 dilution |
|---|---|---|---|---|
| A | Peptide 1 (50) | 0.06 | 0.06 | |
| | Peptide 1 (10) | 0.00 | 0.01 | |
| | Peptide 2 (50) | 0.33 | 0.05 | |
| | Peptide 2 (10) | 0.27 | 0.01 | ↓ |
| | Peptide 3 (50) | 0.25 | 0.05 | <0.04 |
| | Peptide 3 (10) | 0.11 | 0.01 | ↑ |
| | Polyarginine (20) | 0.82 | 0.10 | |
| | Polyarginine (10) | 0.80 | 0.08 | |
| B | Peptide 1 (50) | 0.06 | 0.04 | |
| | Peptide 2 (50) | 0.32 | 0.03 | |
| | Peptide 3 (50) | 0.05 | 0.04 | |

*Part A: Peptides untreated. HPmAb is reactive with peptides 2,3 (untreated) and with polyarginine. Part B: Peptides amino-ethylated to block formation of disulfide bonds between cysteinyl residues. Amino-ethylation of peptides results in elimination of reactivity of HPmAb with peptide 3 and no change in reactivity of peptide 1 or 2. Control mAb (anti-myosin) and nonimmunized mouse serum are not reactive with the peptides or with polyarginine.

The high reactivity of HPmAb with polyarginine (Table IIIA) supports the proposition that the recognition is dependent upon clustered arginyl residues and suggests that other amino acids are not essential for recognition of the epitope. Peptide 1 shows no reactivity with HPmAb, suggesting that a cluster of two arginyl residues is inadequate for recognition while the modest, but real, reactivity of peptide 2 suggests that a density of four arginyl residues, including a cluster of three, within a six residue piece is recognized (Table IIIA). The apparent inconsistency of the display of reactivity by peptide 3 (Table IIIA), in which the four arginyl residues are single, was readily resolved. When the synthetic peptides were used as synthesized, i.e., not treated to block the cysteine—cysteine crosslinkage, peptide 3 showed reactivity with HPmAb. However, when the three peptides were treated, as in the preparation of the protamines (see Section 6.1.2), to block the formation of disulfide bonds between the cysteinyl residues, the reactivity of peptide 3 with HPmAb was eliminated (Table IIIB). We interpret that observation to indicate that, in the untreated state, the two cysteinyl residues in peptide 3 are crosslinked, resulting in a conformation in which the four single arginyl residues are brought into juxtaposition so that those residues are in adequate proximity or orientation for antibody recognition to take place. With the cysteinyl residues blocked, that conformation was not induced and peptide 3 was not reactive with HPmAb (Table IIIB). Consonant with that observation, the reactivity of peptide 2, putatively dependent upon a density of four arginyl residues including a triplet, and the absence of reactivity of peptide 1 were not altered by treatment to block cysteine-cysteine crosslinkage (Table IIIB).

The specific requirement of the HPmAb for an epitope including an arginine triplet was further documented when the HPmAb displayed no reactivity against the more prevalent set of basic nuclear proteins, the histones and, specifically, against the arginine-rich histone H3, in which there are two arginine doublets, residues 52, 53, and 128, 129, but no arginine triplet (DeLange, R. J., et al., 1972, Proc. Natl. Acad. Sci. U.S.A. 69:882).

The possibility that recognition by HPmAb of a cluster of three or more arginyl residues is due solely or mainly to a concentrated high positive charge was probed further by comparing the reactivity of HPmAb with polyarginine, representing maximal net positive charge as well as maximal arginine density, with that of polylysine, representing very nearly as high net positive charge (FIG. 3). The assay data of FIG. 3 indicate that the specificity of the HPmAb is not that of recognition of an epitope with high positive charge but is related to unique properties inherent in a cluster of arginyl residues.

Comparison of the reactivity curves (FIGS. 3 and 4) indicates greater similarity in the binding kinetics of HPmAb with P1 and polyarginine than with P1 and P2. For both P1 and polyarginine, HPmAb appears to be saturated at low antigen concentration. For polyarginine, that saturation might be postulated to be due to a higher order of reiteration of the epitope, but in both P1 and P2 the putative minimum epitope of six amino acids (Geysen, H. M., et al., 1987, Science 235:1184), in this instance a six amino acid piece with four arginyl residues including a cluster of three, appears twice. The greater reactivity of HPmAb with P1 (FIG. 4), therefore, may be due to the cluster of six arginyl residues, a density of arginine not present in P2 (Table IIA).

An overview of the foregoing data leads to the proposition that the HPmAb reacts with clustered arginyl residues, with activity strength related to arginine density, with a minimum requirement of four within a six residue epitope with three of the arginyl residues in series or in juxtaposition to provide a specific configuration or cluster of three arginyl residues.

6.2.4. Protamine-Reactive IgM Antibodies Present in Normal Human Serum

The properties of the human serum protamine-reactive IgM antibodies (Table I) were investigated by comparison with those established for HPmAb and by determining whether the reactivity resides in a specific subset of human IgM antibodies.

The relative reactivities of a representative group of human sera (adult male, adult female, and pediatric) with P1 and P2 and polyarginine were assayed (FIG. 5). Despite the expected differences in absolute titer, the similarity among the sera in rank order of activity with the three antigens, in the slopes of serum dilution versus reactivity curves and in the response to increasing antigen concentration suggests that the serum reactivity is that of a discrete set of IgM antibodies present in all normal sera. The data of FIG. 5 also confirm that the protamine-reactive IgM antibody set of pediatric sera has the same properties as that of adult sera.

Concordance between the immuno-recognition properties of the human IgM antibodies and those of the HPmAb was demonstrated by competition ELISA (FIG. 6). The inhibition by HPmAb of the serum antibody reactivity with both P1 and P2 was proportionate to the concentration of HPmAb. Nearly 50% inhibition of the serum reactivity with P1 was achieved by HPmAb dilution of 1:1,000. Consonant with the observation that the HPmAb displays greater reactivity with P1 than with P2 (FIGS. 2B and 4), the data of FIG. 6 also indicate that the HPmAb displays greater competition with the P1 reactivity of the serum antibodies than with the P2 reactivity.

Assurance that the blocking of the serum IgM reactivity with P1 and P2 was due to specific epitope recognition by the HPmAb was provided by parallel assays carried out with a mouse mAb to chick myosin and with normal (nonimmunized) mouse serum, with no inhibition of human serum IgM reactivity with P1 and P2 exhibited by either.

The converse competition assay, i.e., blocking of the HPmAb with human serum, also indicated that the epitope recognized by the HPmAb displays homology with that recognized by the human protamine-reactive IgM antibodies (Table IV).

TABLE IV

COMPETITION BY HUMAN SERA (ADULT MALE, ADULT FEMALE, PEDIATRIC) WITH REACTIVITY OF HPmAb AGAINST (A) P1 (10 μg/ml) AND (B) P2 (10 μg/ml)*

| | | HPmAB (1:1,000 dilution) | | HPmAB (1:10,000 dilution) | |
|---|---|---|---|---|---|
| Experiment | Serum (1:100 dilution) | OD† | % Decrease | OD† | % Decrease |
| A | 0 | 0.79 | — | 0.74 | — |
| | Adult Male | 0.71 | 10 | 0.65 | 12 |
| | Adult Female | 0.70 | 12 | 0.65 | 12 |
| | Pediatric | 0.68 | 14 | 0.63 | 15 |
| B | 0 | 0.64 | — | 0.57 | — |
| | Adult Male | 0.61 | — | 0.53 | — |
| | Adult Female | 0.62 | — | 0.51 | 11 |
| | Pediatric | 0.58 | 10 | 0.51 | 11 |

*ELISA protocol was modified by the insertion of a single step: before addition of HPmAb, 50 μl of human serum was added to each well, and after 1 hour (at room temperature), the serum was removed and the wells were washed. The reactivity was detected by binding to peroxidase-conjugated anti-mouse IgA, IgG, IgM.
†OD: optical density Although the maximum inhibition by human serum that was displayed in the solid-phase blocking assay used in this study was only ~15% (Table IV), similar blocking activity was effected by a representative serum from each of the human population classes, adult male, adult female, and pediatric. That observation is in accord with the display of similar discrimination and activity of adult and pediatric sera with the synthetic peptides used to define the epitope for HPmAb (compare Tables III and V).

TABLE V

REACTIVITY ($OD_{490}$) OF HUMAN SERA IgM WITH SYNTHETIC PEPTIDES (OF TABLE II): (A) PEPTIDES UNTREATED (B) PEPTIDES AMINO-ETHYLATED*

| | | Serum | | | | | |
|---|---|---|---|---|---|---|---|
| | | Adult Male | | Adult Female | | Pediatric | |
| Experiment | Peptide | 1:100 | 1:500 | 1:100 | 1:500 | 1:100 | 1:500 |
| A | Peptide 1 | 0.12 | 0.09 | 0.02 | 0 | 0.07 | 0.02 |
| | Peptide 2 | 0.72 | 0.24 | 0.70 | 0.29 | 0.63 | 0.19 |
| | Peptide 3 | 0.82 | 0.24 | 0.47 | 0.18 | 0.56 | 0.20 |
| B | Peptide 1 | 0.06 | 0.02 | ND | ND | ND | ND |
| | Peptide 2 | 0.78 | 0.24 | ND | ND | ND | ND |
| | Peptide 3 | 0.05 | 0.01 | ND | ND | ND | ND |

*Serum dilutions are shown above each column. Human serum IgM antibodies are not significantly reactive with peptide 1 untreated or treated, are reactive with peptide 2 when both untreated and treated, and are reactive with peptide 3 untreated, but not when the peptide is treated to prevent cysteine-cysteine crosslinkage (see Table III).
ND: not determined.

The data of Table V, showing that the reactivity of the serum antibodies with the synthetic peptides parallels that of the HPmAb, also provide further support for the consideration that the epitopes for the two categories of antibodies are similar. The IgM antibodies of all three sera recognized, as did the HPmAb (Table III), peptide 2 in either ethylated or nonethylated state (cysteine-cysteine crosslinkage blocked or unblocked), did not recognize peptide 1 in either state, and recognized peptide 3 when nonethylated, but not when ethylated (Table V).

To assure that the serum reactivity with protamines is attributable to a circumscribed set of IgM antibodies, a series of affinity absorption procedures was carried out. First, it was demonstrated that those antibodies distinguish between a fraction of pooled protamines and a fraction of sperm membrane proteins which, as shown previously (Rodman, T. C., et al., 1985, Science 228:1211), includes eight or nine proteins that are reactive with naturally occurring human serum antibodies. After absorption on an affinity column to which ascending amounts of pooled protamines were bound, the serum reactivity with protamines was progressively reduced to zero while only minor reduction of serum reactivity with the sperm membrane protein fraction was observed (FIG. 7).

As in the analysis of the epitope for the HPmAb, the possibility was considered that the reactivity of the serum antibodies was primarily that of a charge-dependent reaction. Also, since autoantibodies to histones have been identified in both normal and pathologic human sera (Shoenfeld, Y., et al., 1987, Arthritis Rheum. 30:169) an assessment was made of the ability of human serum IgM antibodies to discriminate between protamines and histones. In affirmation of the high sensitivity of the ELISA method used in this study (Pruslin, F. H., et al., 1986, J. Immunol. Methods 94:99; Rodman, T. C., et al., 1986, J. Immunol. Methods 94:105), a high titer of IgM antibodies reactive with purified calf thymus histones was detected in the test serum (FIG. 8A). After absorption of an aliquot of the serum on a histone bound affinity column, however, that reactivity was eliminated while reactivity of the histone-absorbed serum against protamines was virtually unchanged (FIG. 8, B and C).

Figure 9B:
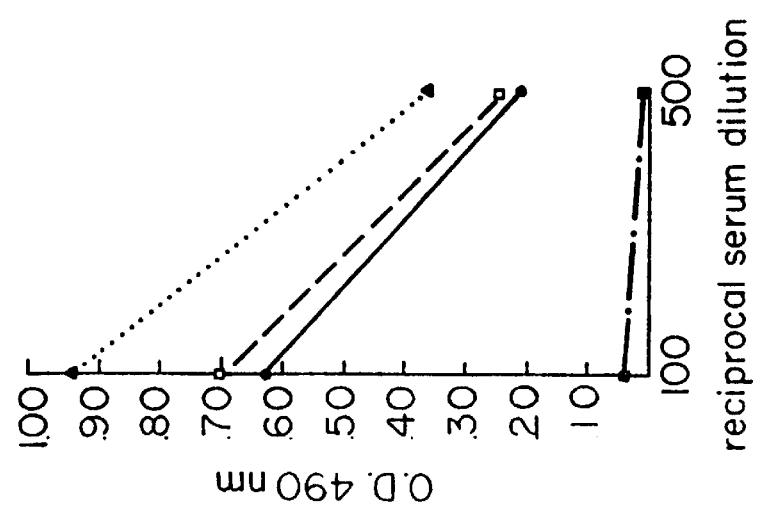
Figure 9C:
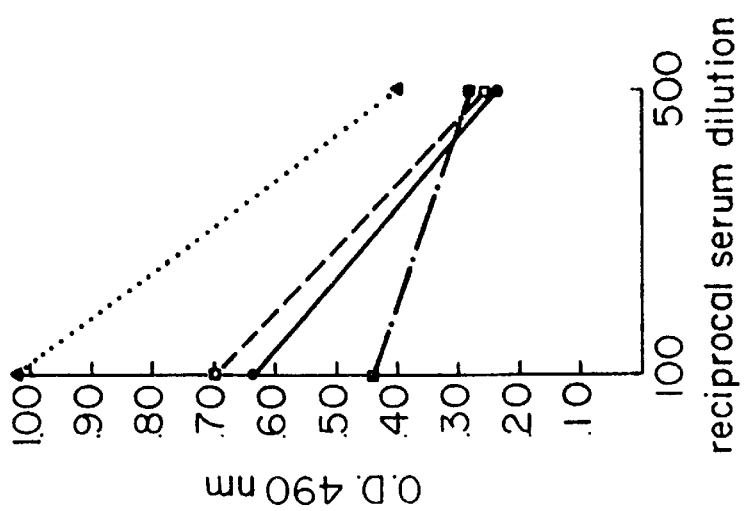

Further assurance that the protamine reactivity of a subset of IgM antibodies in human serum is not that of charge attraction was obtained by the data of FIG. 9. When tested with polylysine, IgM antibodies of human serum did bind to that antigen. However, when the serum was absorbed on a polylysine-bound affinity column, reactivity with polylysine was deleted while reactivity with protamines and with polyarginine was retained (FIG. 9B). Conversely, when the serum was absorbed on polyarginine, reactivity with polylysine was retained while reactivity with protamine 1, portamine 2 and polyarginine was deleted (FIG. 9C).

6.2.5. Antigenic Sites Recognized by HpmAb and Human Serum Immunoglobulin Antibodies are Similar and Perhaps Identical Table VI is a summary comparison of the reactivity of HPmAb, a mouse anti-protamine IgG secreted by a hybridoma of reasonably assured monoclonality (see Section 6.1.3) and the reactivity of a specific subset of IgM antibodies in human sera.

TABLE VI

SUMMARY OF CONCORDANCE OF ANTIGEN RECOGNITION BY HPmAb AND PROTAMINE-REACTIVE SERUM IgM ANTIBODIES

| | | ELISA | Protamine- |
|---|---|---|---|
| Antigen | HPmAB | Total serum IgM | reactive serum IgM |
| P1 | ++ | + | |
| P2 | + | ++ | |
| Polyarginine | ++ | ++ | |
| Polylysine | − | + | —* |
| Peptide 1 | − | − | |
| Peptide 1, ethylated | − | − | |
| Peptide 2 | + | + | |
| Peptide 2, ethylated | + | + | |
| Peptide 3 | + | + | |
| Peptide 3, ethylated | − | − | |
| Pooled calf thymus histones | − | + | —† |
| Histone H3 | − | + | —§ |
| Sperm membrane proteins | − | + | —\| |

*Serum absorbed on polylysine, polylysine-reactive antibodies deleted, protamine-reactive antibodies retained.
†Serum absorbed on calf thymus histones, histone-reactive antibodies deleted, protamine-reactive antibodies retained.
§By inference from †.
\|Serum absorbed on pooled protamines, protamine-reactive antibodies deleted, sperm membrane protein-reactive antibodies retained.

The comparison (Table VI) indicates that the epitopes for the two antibody sets show a high degree of homology. The principle difference detected by the experimental protocols of this study is that of apparent rank order of reactivity with the three antigens, human sperm protamine 1, human sperm protamine 2, and polyarginine (compare FIGS. 3 and 4 with FIG. 5). One possible explanation for that difference may be that the several subsets of protamine-reactive human IgM antibodies, i.e., those of different binding affinities, have modestly different preferences for intra-epitope arrangement of arginyl residues, or for extra-epitope factors that influence binding patterns (Geysen, H. M., et al., 1987, Science 235:1184; Dryberg, T., and Oldstone, M. B. A., 1986, J. Exp. Med. 164:1344). It is apparent, however, that the dominant and common characteristic of the epitope recognized by both HPmAb and the serum IgM antibodies is that of clustered arginyl residues.

Since the protamine-reactive IgM antibodies are present in sera of pediatric individuals who have had no exposure to sperm or protamines, the possibility was considered that other proteins autogenous to humans with segments homologous to that putative epitope might be related either to origin (immunogenic stimulation) or to role (antigenic recognition) of that set of natural IgM antibodies. A search was made of protein sequence databases for segments of six amino acids with four arginyl residues, including a cluster of three. The results are shown in Table VII.

TABLE VII

PROTEINS, OTHER THAN PROTAMINES AND SPERM-SPECIFIC HISTONES, WITH A SEGMENT OF SIX AMINO ACIDS INCLUDING FOUR ARGINYL RESIDUES, THREE OF WHICH ARE ARRANGED IN A CLUSTER

|  | Protein | Residues |
| --- | --- | --- |
| Human | Complement C3 precursor | 668–673 |
|  | Complement C4A | 1,426–1,431 |
|  | T cell surface glycoprotein CD8 precursor | 208–213 |
|  | T cell surface glycoprotein CD4 precursor | 422–427 |
|  | Inferred precursor of γ chain of histocompatibility antigen |  |
| Bacteria |  |  |
| Escherichia coli | Replication initiation protein | 57–62 |
|  |  | 65–70 |
|  | Transposase | 139–144 |
|  | nus B protein | 3–8 |
|  | 30 S ribosomal protein | 2–7 |
|  | Alanyl-tRNA synthetase | 430–435 |
|  | Diaminopimelate decarboxylase | 403–408 |
|  | DNA-directed RNA polymerase | 197–202 |
|  |  | 1,368–1,373 |
| Serratia marcescens | Anthranilate synthetase (component II) | 157–163 |
| Viruses |  |  |
| Herpes simplex (type 1) | Kinase-related transforming protein | 141–146 |
| Herpes simplex (type 2) | Glycoprotein D | 364–369 |
| Papillomavirus (type 6b) | Probable L2 protein | 4–9 |
| Papillomavirus (type 11) | Probable L2 protein | 3–8 |
|  |  | 438–443 |
| Papillomavirus (type 33) | Probable L2 protein | 450–455 |
|  | Probable E6 protein | 140–145 |
| Papillomavirus (type 8) | Probable L2 protein | 318–323 |
|  |  | 327–332 |
| Hepatitis B virus subtype ayw and 6 subtypes) | Core antigen | 150–155 |
|  |  | 155–160 |
|  |  | 164–169 |
|  |  | 171–176 |
| Epstein-Barr virus (strain B95-8) | Hypothetical BHLF 1 protein | 157–162 |
|  |  | 282–287 |
|  |  | 407–412 |
|  |  | 532–537 |
|  |  | 2,085–2,090 |
|  | Hypothetical BORF 1 protein | 9–14 |
|  | Probable glycoprotein | 528–533 |
|  |  | 837–842 |
|  | Hypothetical BSLF 1 protein | 859–864 |
|  | Hypothetical BLLF 2 protein | 53–58 |
|  | Hypothetical BERF 3 protein | 90–95 |
|  |  | 362–367 |
|  | Hypothetical BRLF 1 protein | 86–91 |
| Adenovirus 2 | Minor core protein | 315–320 |
|  |  | 331–336 |
|  | Probable early E4 34K protein | 265–270 |
|  | Probable early E4 13K protein | 70–75 |
|  | Probable early E1B 21K protein | 157–162 |
|  | Late L1 52K protein | 53–58 |
|  | Early E2A DNA-binding protein | 46–51 |
|  | Major core protein precursor | 100–105 |
|  |  | 152–157 |
|  | Terminal protein | 349–354 |
|  |  | 366–371 |
| Adenovirus 5 | Probable early E1B 21K protein | 157–162 |
|  | Late L1 52K protein | 54–59 |
|  | Early E2A DNA-binding protein | 46–51 |
| Adenovirus 7 | Terminal protein | 338–343 |
|  |  | 355–360 |
| Rhinovirus 2 | Genome polyprotein | 1,396–1,401 |
| Yellow fever virus (strain 17D) | Genome polyprotein | 1,702–1,707 |
| Sindbis virus (two strains) | Structural polyprotein | 22–27 |
|  | Nonstructural polyprotein | 1,886–1,891 |
| T cell leukemia virus (HTLV II) | env polyprotein | 305–310 |
| HIV (HTLV III) | Trans-activating transcriptional Regulatory protein: |  |
|  | version 1 | 61–66 |
|  | version 2 | 39–44 |

The sequence, of six amino acids with four arginyl residues, including a cluster of three, was identified in all of the vertebrate and invertebrate protamines or sperm-specific histones that have been sequenced, in a few bacterial proteins mainly of Escherichia coli, and in a number of viral proteins (Table VII). The only human autogenous proteins displaying that sequence, other than protamines, are two complement precursors, two T cell glycoproteins and one (inferred) variant of the γ chain of class II histocompatibility antigens (Table VII).

6.3. Discussion

We have detected a set of natural IgM antibodies in sera of normal human males and females of all age groups, that are reactive with human protamines, the basic nuclear proteins of sperm, and we have identified the minimum antigenic site of six residues as one with four arginyl residues including a cluster of three. Since those antibodies are present in sera of pediatrics, who have had no exposure to protamines, immunogenic stimulation by protamines as the origin of those antibodies is argued against. Within the context of currently recognized immunologic mechanisms, the origin of those antibodies, therefore, may be attributed to other autogenous molecules with a sequence homologous with the protamine antigenic site or to idiotopes on other immunoglobulins bearing the image of the protamine antigenic site.

The possibility that those antibodies are induced by any of the segments of the human proteins listed in Table VII is intriguing since all are believed to be involved in immunoregulatory mechanisms and all may be present in the nascent immune system. On the other hand, since the neonatal gastro-intestinal tract is populated with E. coli, the possibility that the E. coli proteins (Table VII) provide the initial stimulus for induction of the protamine-reactive antibodies also may be considered. It has been hypothesized that natural antibodies may arise from stimulation by intestinal tract flora (Boyden, S. V., 1966, Adv. Immunol. 5:1).

It is also possible that viral proteins may be the antigenic target of these antibodies. It has been hypothesized that one role of natural antibodies may be that of defense against potential infectious agents (Michael, J. G., et al., 1962, J. Exp. Med. 115:131).

These studies have provided a definition of the antigenic site with which a set of natural IgM antibodies of human sera are reactive.

7. EXAMPLE: LOW AFFINITY PROTAMINE-REACTIVE IgM ANTIBODIES PRESENT IN HUMAN SERA ARE RELATED TO HUMAN IMMUNODEFICIENCY VIRUS LATENCY

In the examples detailed herein, we describe low-affinity binding, anti-protamine IgM antibodies in human sera, whose presence in sera is related to the latency period between Human Immunodeficiency Virus (HIV) infection and the onset of AIDS.

The latency period between infection by HIV and clinical manifestation of AIDS is highly variable, the maximum period has not yet been determined, and it is possible that some HIV infected individuals may never develop the disease. We report here the identification, and method for quantitative determination, of a factor that appears to be indicative of the capacity of an HIV infected individual to withstand the pathogenetic progression to AIDS. That factor is detectable in sera of normal subjects and HIV infected individuals who subsequently exhibit a significant period of latency but is absent or deficient in sera of individuals diagnosed with AIDS and sera of HIV infected individuals who, though asymptomatic at the time of the blood sampling, proceed to AIDS within a relatively short time. That factor is a subset of a population of IgM antibodies reactive with a specific antigenic site characteristic of sperm protamines. The critical subset of protamine-reactive IgM antibodies appears to be natural antibodies. The assay method described herein provides a modality for prediction of the probable period of latency for an HIV infected individual.

7.1. The Presence in Normal and Absence From AIDS Patients' Sera of Low Affinity Protamine-Reactive IgM Antibodies We have found that when normal adult sera are assayed by ELISA with ascending concentrations of protamines, a sharp increase in the slope of the activity (optical density, O.D.) versus serum dilution curve is produced at the higher antigen concentrations (FIG. 10A). Summary curves (FIG. 10B) for a similar assay of 20 randomly selected normal adult sera verified that the increase in slope is not an anomaly of one or a few sera, but is a consistent characteristic of normal adult sera, suggesting that there is, in addition to the principal antibody set, a detectable secondary subset of protamine-reactive IgM antibodies. We tested the possibility whether the secondary subset was one recognizing a different epitope on the protamine molecule, or was one with the same recognition specificity as the principle set but displaying different binding affinities. Comparable assays (FIG. 10C) with the same sera as those tested against protamine using as antigen a synthetic decapeptide (DP), which includes one copy of the antigenic site recognized by the serum protamine-reactive IgM antibodies (see section 6, supra) indicated that the increase in slope of the activity curve for those sera with high antigen concentration was not attributable to a subset with different recognition specificity, but could be interpreted as displaying a subset reactive with the same antigenic site but with demonstrably lower affinity. When a group of 15 sera from patients diagnosed with AIDS was similarly tested against ascending concentrations of protamine, the increase in slope of the reactivity curve at high antigen concentration, interpreted as indicative of a secondary subset of protamine-reactive IgM antibodies, was not seen in any assays (FIG. 11), even in assays of those sera (FIG. 11A) with a high total titer of protamine-reactive IgM antibodies.

7.2. A Quantitation of Anti-Protamine Antibodies For Prediction of HIV Latency Since the presence in normal and absence in AIDS sera of a specific factor suggested the possibility of a disease-related deficiency, a system of computation was devised to quantitate that factor, i.e., to assess the proportionate titer of the secondary subset of protamine-reactive IgM antibodies represented by the increase in slope of the reactivity curve with high antigen concentration. By inspection of the sets of curves (FIG. 10A, B), 2 $\mu$g/ml and 20 $\mu$g/ml were empirically selected as suitable test antigen concentrations. The rise of the curve between two points on the X axis, serum dilutions 1:100 (x1) and 1:500 (x2), may be expressed as the difference between the O.D. values on the Y axis for those two points. The increase in rise from that of the 2 $\mu$g protamine curve to that of the 20 $\mu$g curve is (O.D.x1−O.D.x2) at 20 $\mu$g/ml protamine—(O.D.x1−O.D.x2) at 2 $\mu$g/ml protamine, and may be noted as $\Delta 20-\Delta 2$.

Values for $\Delta 20-\Delta 2$ were computed for the sera of a group of male and female adults from the general population (HIV negative by western blot), a group of patients diagnosed as having AIDS, and a group at risk for AIDS (seropositive male homosexuals) and diagnosed as asymptomatic or mildly immunodeficient (low T4 count or low mitotic stimulation index or both, but no other abnormality) at the time the blood specimen was obtained. For some of the latter, a follow-up clinical assessment was available as noted. The results are shown in FIG. 12.

By inspection of FIG. 12A, a value of 15 was considered to be the lower limit of "normal" range. On that basis, the percent of each group of sera within the normal range was determined (Table VIII).

TABLE VIII

PERCENTAGE OF SERA WITHIN THE NORMAL RANGE OF ANTI-PROTAMINE IgM LEVELS FOR EACH PATIENT GROUP

| | Group | Total | % in normal range |
|---|---|---|---|
| A | normal | 57 | 95 |
| B | AIDS | 31 | 6 |
| C | asymptomatic → AIDS | 14 | 0 |
| D | asymptomatic → asymptomatic | 10 | 90 |
| E | asymptomatic → fate unknown | 10 | 50 |

The data displayed in FIG. 12 indicate that a $\Delta 20-\Delta 2$ value within the normal range in an HIV positive serum is predictive of a latency period of at least two years before the manifestation of AIDS, and probably longer, while a low $\Delta 20-\Delta 2$ value is predictive that progression to the disease is imminent.

The fact that the values for groups A and D and those for groups B and C comprise two distinct distributions while the values for group E include both distributions (FIG. 12) suggests that the set of intervals between HIV seropositivity and AIDS manifestation for each of groups C and D is characteristic and relevant.

7.3. Confirmation of the Existence of a Low-Affinity Subset of Protamine-Reactive Antibodies The subset of protamine-reactive IgM antibodies represented by $\Delta 20-\Delta 2$ has been distinguished as "low affinity."

Antibody affinity is an expression of the strength with which the antibody binds to an antigen that it recognizes. That binding is dependent upon the composite effect of the intermolecular forces, e.g., hydrogen bonding, hydrophobicity, ionic interaction (Karush, F., 1962, Adv. Immunol. 2:1–40). A measure of the binding strength may be made for the binding of homogeneous antibody to a hapten or single antigenic determinant and, by application of the Law of Mass Action, expressed as the Affinity Constant. The Affinity Constant, therefore, is directly related to resistance to dissociation of the antibody/antigen complex.

Since it is known that a series of antibodies of different affinities arises in response to a single immunologic induction (Werblin, T. P., et al., 1972, Immunochem. 9:987–1011), much attention has been given and many methods devised to determine the separate "apparent" affinity constants of a population of antibodies reactive with the same antigenic determinant (Steensgaard, J., et al., 1980, Mol. Immunol. 17:689–698; Lew, A. M., 1984, J. Immunol. Meth. 72:171–176; Sciutto, E., et al., 1987, Mol. Immunol. 24:577–585). While those methods and their applications have been controverted and defended, a useful empirical principle has emerged: In an antibody system heterogeneous for affinity, those antibodies of high affinity will bind to antigen and resist dissociation from antigen more successfully than antibodies of low affinity. Therefore, antibody subpopulations of different affinities for the same antigen may be identified by allowing a fixed volume of the antibody mixture (e.g., serum) to react with increasing amounts of antigen. As concentration of antigen increases, high affinity antibodies are saturated and antibodies of lower affinity will react with antigen. The experimental evidence has also shown that such antibody series frequently have unimodal or bimodal affinity distributions, with one or two major subpopulations (Gandolfi, A., et al., 1981, Theor. Biol. 92:57–84). In accordance with that principle, the subset of antibodies represented by $\Delta 20-\Delta 2$, i.e., that detected at high antigen concentration, may be considered to represent a population of lower affinity than the principal population, detected at lower antigen concentrations.

Confirmatory evidence for the inference that the $\Delta 20-\Delta 2$ value represents a subset of lower affinity than the main population of protamine-reactive IgM antibodies was obtained by carrying out the binding reaction in elevated NaCl molarity, which eliminates the phase of antibody binding due to ionic interaction. The assay serum diluent was adjusted from 0.15M NaCl to 0.3M NaCl. The reactivity curves for the assays carried out in that medium (FIG. 10D) show that the increase in rise of the curve at high antigen concentration (FIGS. 10A, 10B) was eliminated and the $\Delta 20-\Delta 2$ values were markedly reduced. Elimination of the phase of antibody binding due to ionic interaction, considered to be a low energy component of binding (Karush, F., 1962, Adv. Immunol. 2:1–40) appeared to result in preferential elimination of the binding of the low affinity subset of antibodies (FIGS. 10A, 10D).

7.4. Pediatric Sera Contain a Population of Protamine-Reactive IgM Antibodies That is Homogeneous in Binding Affinity As described in Section 6, supra, sera of clinically normal pediatric subjects contain protamine-reactive IgM antibodies with the same antigen recognition specificity as those of adult sera. When pediatric sera were assayed with ascending concentrations of P2 (FIG. 13A) and DP, (FIG. 13B) the parallelism of the curves indicated that, unlike the normal adult sera, the protamine-reactive IgM antibodies of the pediatric sera are a homogeneous (or unimodal) population with respect to binding affinity.

7.5. Naturally Occurring Anti-Protamine Antibodies

The anti-protamine antibodies detected in pediatric sera cannot be attributed to immunogenic stimulation by protamine since protamines are synthesized de novo in the post-puberal testis and are incorporated into the nuclei of no cells other than those of the spermiogenic series. Nor may the protamine-reactive IgM antibodies detected in the sera of the 12 or more day old neonates (see Section 6, supra) be attributed to maternal origin since IgM does not cross the placenta. The identified antigenic site for the protamine-reactive antibodies has very limited occurence in human endogenous proteins other than protamines (see Section 6.2.5, supra). It is reasonable, therefore, to infer that the protamine-reactive IgM antibodies of the pediatric sera are natural antibodies and, by extrapolation, one of the two subsets of the protamine-reactive IgM antibodies of the adult sera consists of natural antibodies.

Protamines are sequestered from the immune system during their synthesis and cellular incorporation (Dym, M. and Fawcett, D. W., 1970, Biol. Reprod. 3:308–326) and we have shown that protamines are non-immunosuppressive, i.e., they do not inhibit T-cell mitogenesis in vitro as do other sperm-derived proteins (Rodman, T. C., et al., 1985, Science 228:1211–1215). Therefore, the sera of post-puberal males and sexually experienced females may contain some protamine-reactive antibodies that may be attributable to immunogenic induction by protamines. Thus, we postulate that the protamine-reactive IgM antibodies of adult human sera include two subsets differing in origin: (1) natural antibodies, and (2) induced antibodies.

The foregoing discussion and our experimental results indicate that the protamine-reactive antibodies of pediatric sera are natural antibodies, and suggest that the natural protamine-reactive antibodies of pediatric sera correspond to the low affinity subset of protamine-reactive IgM antibodies of adult sera.

We propose that the deficiency of the low affinity (potentially natural) subset of protamine-reactive antibodies in HIV positive sera (FIGS. 11, 12) may be related to the pathogenetic progression to AIDS either as an index or as a contributory factor.

The assay method described herein provides a modality for predicting the likely period of latency for an HIV infected individual. Such information may be useful in the medical management of individual patients, in projection of community needs for medical care facilities and, most urgently, in the selection of appropriate subjects for trial of proposed therapeutic agents.

8. DEPOSIT OF HYBRIDOMA

Hybridoma cell line HPmAb, producing anti-protamine monoclonal antibody HPmAb, has been deposited with the American Type Culture Collection, Rockville, Md., and has been assigned acession number HB 9668.

The present invention is not to be limited in scope by the cell line deposited since the deposited embodiment is intended as a single illustration of one aspect of the invention and any cell lines which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed is:

1. An isolated, low affinity binding human IgM antibody immunoreactive with a human protamine 2 epitope comprising a six amino acid residue sequence including at least four arginyl residues, three of said arginyl residues being adjacent residues, and wherein said low affinity binding antibody is identifiable by a method comprising the steps of
    a. providing a plurality of solid supports coated with a high concentration and a low concentration of said human protamine 2, wherein said high concentration is 10 fold greater than said low concentration;
    b. providing a serum sample suspected of containing said low affinity binding human IgM antibody and diluting said serum sample 1:100 and 1:500;
    c. separately contacting said solid supports with said dilutions in the presence of 0.15M NaCl under conditions wherein any said low affinity binding human IgM antibody in said dilution binds to said protamine 2 to form IgM:protamine 2 complexes;
    d. measuring said IgM:protamine 2 complexes; and
    e. producing a reactivity curve correlating said IgM:protamine 2 complexes to said protamine 2 concentration for each said dilution, wherein said low affinity binding human IgM antibody is present if there is an increase in slope of said reactivity curve between said serum dilution 1:100 and 1:500 at said high antigen concentration relative to any increase in slope of said reactivity curve between said serum dilution 1:100 and 1:500 at said low antigen concentration.

2. The isolated, low affinity binding human IgM antibody of claim 1 wherein said epitope is specifically bound by a monoclonal antibody produced by the hybridoma having ATCC accession No. HB 9668.

3. The isolated, low affinity binding human IgM antibody of claim 1 wherein said antibody is a natural antibody.

4. A method for determining the latency for development of AIDS in an HIV-infected human comprising the steps of
    a. obtaining a serum sample from said human;
    b. obtaining a serum sample from a non-HIV infected human;
    c. diluting said serum samples obtained in steps a and b 1:100 and 1:500;
    d. providing a plurality of solid supports coated with a high and a low concentration of an antigen comprising an epitope found on human protamine 2, comprising a six amino acid residue including at least four arginyl residues, three of said arginyl residues being adjacent, which epitope is specifically bound by a monoclonal antibody produced by the hybridoma having ATCC accession No. HB 9668, and wherein said high concentration is 10 fold greater than said low concentration;
    e. separately contacting said solid supports with said dilutions under conditions wherein any low affinity binding human IgM antibody in said dilution binds to said antigen to form IgM:antigen complexes;
    f. measuring said IgM:antigen complexes; and
    g. producing a reactivity curve correlating said IgM:antigen complexes to said antigen concentration for each said dilution for each said serum sample, wherein the presence or amount of said low affinity binding human IgM antibody is correlated to an increase in slope of said reactivity curve between said serum dilution 1:100 and 1:500 at said high antigen concentration relative to any increase in slope of said reactivity curve between said serum dilution 1:100 and 1:500 at said low antigen concentration; and,
    h. comparing the amount of said low affinity binding human IgM antibody in said serum sample from said HIV-infected human with that obtained from said non-HIV infected human, wherein said HIV-infected human will have a latency period of at least two years before developing AIDS if the amount of said low affinity binding human IgM antibody present in said serum sample from said HIV-infected human is equal to or greater than the amount of said low affinity binding human IgM antibody in said serum from said non-HIV infected human.

5. An ELISA kit for determining the latency for development of AIDS in a human, said kit comprising in one or more containers:
    a. a protein or peptide comprising an epitope found on human protamine 2, comprising a six amino acid residue including at least four arginyl residues, three of said arginyl residues being adjacent, which epitope is specifically bound by a monoclonal antibody produced by the hybridoma having ATCC accession No. HB 9668; and
    b. an anti-human IgM antibody conjugated to a detectable enzyme label.

6. The kit of claim 5 wherein said protein or peptide is immobilized.

* * * * *